(12) United States Patent
Ankenbauer et al.

(10) Patent No.: US 7,759,107 B2
(45) Date of Patent: Jul. 20, 2010

(54) THERMOSTABLE NUCLEIC ACID POLYMERASE FROM THERMOCOCCUS GORGONARIUS

(75) Inventors: Waltraud Ankenbauer, Penzberg (DE); Vitaly Svetlichny, Bayreuth (DE); Elizaveta Bonch-Osmolovskaya, Moscow (RU); Christine Ebenbichler, Antdorf (DE); Bernhard Angerer, Rosenheim (DE); Gudrun Schmitz-Agheguian, Bernried (DE); Frank Laue, Paehl-Fischen (DE)

(73) Assignee: Roche Diagnostics GmbH, Mannheim (DE)

( * ) Notice: Subject to any disclaimer, the term of this patent is extended or adjusted under 35 U.S.C. 154(b) by 7 days.

(21) Appl. No.: 12/135,994

(22) Filed: Jun. 9, 2008

(65) Prior Publication Data

US 2009/0093043 A1 Apr. 9, 2009

Related U.S. Application Data

(62) Division of application No. 09/269,860, filed as application No. PCT/EP97/05393 on Oct. 1, 1997, now Pat. No. 7,425,423.

(30) Foreign Application Priority Data

Oct. 3, 1996 (EP) ................................. 96115874
Jan. 16, 1997 (EP) ................................. 97100584

(51) Int. Cl.
  C12N 9/12 (2006.01)
  C12N 1/20 (2006.01)
  C12Q 1/48 (2006.01)
(52) U.S. Cl. .................... 435/252.3; 435/194; 435/183; 435/320.1; 536/23.1; 536/23.2
(58) Field of Classification Search ........................ None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 4,889,818 A | 12/1989 | Gelfand et al. |
| 5,322,785 A | 6/1994 | Comb et al. |
| 5,352,778 A | 10/1994 | Comb et al. |
| 5,436,149 A | 7/1995 | Barnes |

FOREIGN PATENT DOCUMENTS

| | | |
|---|---|---|
| EP | 0 455 430 A2 | 11/1991 |
| EP | 0 201 184 B1 | 12/1992 |
| EP | 0 200 362 B1 | 1/1993 |
| EP | 0 547 920 A2 | 6/1993 |
| EP | 0 546 920 B1 | 3/1997 |
| EP | 0 258 017 B1 | 6/1997 |
| EP | 0 693 078 B1 | 6/1999 |
| WO | WO 94/26766 | 11/1994 |

OTHER PUBLICATIONS

Balch et al., "Methanogens: Reevaluation of a Unique Biological Group", *Microbiological Reviews*, 1979,43:260-296.
Bernad et al., "A Conserved 3'-5' Exonuclease Active Site in Prokaryotic and Eukaryotic DNA Polymerases", *Cell*, 1989, 59:2 19-228.
Bessman et al., "Enzymatic Synthesis of Deoxyribonucleic Acid", *Journal of Biological Chemistry*, 1957, 233:171-177.
Braithwaite and Ito, "Compilation, alignment, and phylogenetic relationships of DNA Polymerases", *Nucleic Acids Research*, 1993, 21:787-802.
Brinkmann et al., "High-level expression of recombinant genes in *Escherichia coli* is dependent on the availability of the *dnaY* gene product", *Gene*, 1989, 85:109-114.
Buttin and Kornberg, "Enzymatic Synthesis of Deoxyribonucleic Acid", *Journal of Biological Chemistry*, 1966, 241:5419-5427.
Cariello et al., "Fidelity of *Thermococcus litoralis* DNA polymerase (Vent™) in PCR determined by denaturing gradient gel electrophoresis", *Nucleic Acids Research*, 1991, 19:4193-4198.
Chien et al, "Deoxyribonucleic Acid Polymerase from the Extreme Thermophile *Thermus aquaticus*", *Journal of Bacteriology*, 1976, 127:1550-1557.
Flaman et al., "A rapid PCR fidelity assay", *Nucleic Acids Research*, 1994,22: 3259-3260.
Frey and Suppmann, "Demonstration of the Expand™ PCR System's Greater Fidelity and Higher Yields with a *lacI*-based PCR Fidelity Assay", *Biochemica*, 1995, 2:8-9.
Frey and Suppmann, ."Demonstration of the Expand™ PCR System's Greater Fidelity and Higher Yields with a lad-based PCR Fidelity Assay", *Biochemica Information*, 1995, 96:21-23.
Höltke et al., "Sensitive Chemiluminescent Detection of Digoxigenin-Labeled Nucleic Acids: A Fast and Simple Protocol and Its Applications", *Biotechniques*, 1992, 12:104-113.
Keohavong and Thilly, "Fidelity of DNA polymerases in DNA amplification", *Proceedings of National Academy of Science USA*, 1989, 86:9253-9257.
Lawyer et al., "Isolation, Characterization and Expression in *Escherichia coli* of the DNA Polymerase Gene from *Thermus aquaticus*", *The Journal of Biological Chemistry*, 1989, 264:6427-6437.
Lehman et al., "Enzymatic Synthesis of Deoxyribonuecleic Acid", *The Journal of Biological Chemistry*, 1958, 233:163-170.

(Continued)

Primary Examiner—Richard G Hutson
(74) Attorney, Agent, or Firm—Townsend and Townsend and Crew LLP

(57) ABSTRACT

A purified thermostable enzyme is derived form the thermophilic archaebacterium *Thermococcus gorgonarius*. The enzyme can be native or recombinant, retains approximately 90% of its activity after incubation for two hours at 95° C. in the presence of stabilizing agents and possesses 3'-5' proofreading exonuclease activity. Thermostable DNA polymerases are useful in many recombinant DNA techniques, especially nucleic acid amplification by the polymerase chain reaction (PCR).

13 Claims, 16 Drawing Sheets

OTHER PUBLICATIONS

Ling et al., "Optimization of the Polymerase Chain Reaction with Regard to Fidelity: Modified T7. *Taq*, and Vent DNA Polymerases", *PCR Methods and Applications*, 1991, 1:63-69.

Lundberg et al., "High-fidelity amplification using a thermostable DNA polymerase isolated from *Pyrococcus furiosus*", Gene, 1991, 108:1-6.

Mattila et al., "Fidelity of DNA synthesis by the *Thermococcus litoralis* DNA polymerase—an extremely heat stable enzyme with proofreading activity", *Nucleic Acids Research*, 1991, 19:4967-4973.

Ochman et al., Amplification of Flanking Sequences by Inverse PCR, *PCR Protocols: A Guide to Methods and Applications*, 1990, pp. 219-227.

Provost et al., "Transgenic systems for in vivo mutation analysis", *Mutation Research*, 1993, 288:133-149.

Raleigh et al., "McrA and McrB restriction phenotypes of some *E. coli* strains and implications for gene cloning", *Nucleic Acids Research*, 1988, 16:1563-1575.

Rosenberg et al., "Vectors for selective expression of cloned DNAs by T7 RNA polymerase", *Gene*, 1987, 56: 25-135.

Spanos and Hübscher, "Recovery of Functional Proteins in Sodium Dodecyl Sulfate Gels", *Methods in Enzymology*, 1983, 91:263-277.

Studier et al., "Use of T7 RNA Polymerase to Direct Expression of Cloned Genes", *Methods in Enzymology*, 1990, 185:60-89.

SEQ ID NO. 6:

```
ATG ATC CTC GAT ACA GAC TAC ATA ACT GAG GAT GGA AAG CCC GTC ATC   48
TAC TAG GAG CTA TGT CTG ATG TAT TGA CTC CTA CCT TTC GGG CAG TAG   48
 M   I   L   D   T   D   Y   I   T   E   D   G   K   P   V   I   16

AGG ATC TTC AAG AAG GAG AAC GGC GAG TTC ACC ATA GAC TAC GAC AGA   96
TCC TAG AAG TTC TTC CTC TTG CCG CTC AAG TGG TAT CTG ATG CTG TCT   96
 R   I   F   K   K   E   N   G   E   F   T   I   D   Y   D   R   32

AAC TTT GAG CCA TAC ATC TAC GCG CTC TTG AAG GAC GAC TCT CCG ATT  144
TTG AAA CTC GGT ATG TAG ATG CGC GAG AAC TTC CTG CTG AGA GGC TAA  144
 N   F   E   P   Y   I   Y   A   L   L   K   D   D   S   P   I   48

GAG GAC GTC AAG AAG ATA ACT GCC GAG AGG CAC GGC ACT ACC GTT AGG  192
CTC CTG CAG TTC TTC TAT TGA CGG CTC TCC GTG CCG TGA TGG CAA TCC  192
 E   D   V   K   K   I   T   A   E   R   H   G   T   T   V   R   64

GTT GTC AGG GCC GAG AAA GTG AAG AAG AAG TTC CTA GGC AGG CCG ATA  240
CAA CAG TCC CGG CTC TTT CAC TTC TTC TTC AAG GAT CCG TCC GGC TAT  240
 V   V   R   A   E   K   V   K   K   K   F   L   G   R   P   I   80

GAG GTC TGG AAG CTC TAC TTC ACT CAC CCC CAG GAC GTT CCC GCA ATC  288
CTC CAG ACC TTC GAG ATG AAG TGA GTG GGG GTC CTG CAA GGG CGT TAG  288
 E   V   W   K   L   Y   F   T   H   P   Q   D   V   P   A   I   96
```

*FIG. 3*

```
AGG GAC AAG ATA AAG GAG CAT CCT GCC GTT GTG GAC ATC TAC GAG TAC  336
TCC CTG TTC TAT TTC CTC GTA GGA CGG CAA CAC CTG TAG ATG CTC ATG  336
 R   D   K   I   K   E   H   P   A   V   V   D   I   Y   E   Y   112

GAC ATC CCC TTC GCG AAG CGC TAC CTC ATA GAC AAA GGC TTA ATC CCG  384
CTG TAG GGG AAG CGC TTC GCG ATG GAG TAT CTG TTT CCG AAT TAG GGC  384
 D   I   P   F   A   K   R   Y   L   I   D   K   G   L   I   P   128

ATG GAG GGC GAC GAG GAA CTT AAG ATG CTC GCC TTC GAC ATC GAG ACG  432
TAC CTC CCG CTG CTC CTT GAA TTC TAC GAG CGG AAG CTG TAG CTC TGC  432
 M   E   G   D   E   E   L   K   M   L   A   F   D   I   E   T   144

CTC TAT CAC GAG GGC GAG GAG TTC GCC GAA GGG CCT ATC CTG ATG ATA  480
GAG ATA GTG CTC CCG CTC CTC AAG CGG CTT CCC GGA TAG GAC TAC TAT  480
 L   Y   H   E   G   E   E   F   A   E   G   P   I   L   M   I   160

AGC TAC GCC GAC GAG GAA GGG GCG CGC GTT ATT ACC TGG AAG AAT ATC  528
TCG ATG CGG CTG CTC CTT CCC CGC GCG CAA TAA TGG ACC TTC TTA TAG  528
 S   Y   A   D   E   E   G   A   R   V   I   T   W   K   N   I   176

GAC CTT CCC TAT GTC GAC GTC GTT TCC ACC GAG AAG GAG ATG ATA AAG  576
CTG GAA GGG ATA CAG CTG CAG CAA AGG TGG CTC TTC CTC TAC TAT TTC  576
 D   L   P   Y   V   D   V   V   S   T   E   K   E   M   I   K   192

CGC TTC CTC AAG GTC GTC AAG GAA AAG GAT CCC GAC GTC CTC ATA ATC  624
GCG AAG GAG TTC CAG CAG TTC CTT TTC CTA GGG CTG CAG GAG TAT TAG  624
 R   F   L   K   V   V   K   E   K   D   P   D   V   L   I   I   208
```

*FIG. 3*
(Continued)

```
TAC AAC GGC GAC AAC TTC GAC TTC GCC TAC CTC AAG AAG CGC TCC GAG  672
ATG TTG CCG CTG TTG AAG CTG AAG CGG ATG GAG TTC TTC GCG AGG CTC  672
 Y   N   G   D   N   F   D   F   A   Y   L   K   K   R   S   E   224

AAG CTC GGA GTC AAG TTC ATC CTC GGA AGG GAA GGG AGC GAA CCG AAA  720
TTC GAG CCT CAG TTC AAG TAG GAG CCT TCC CTT CCC TCG CTT GGC TTT  720
 K   L   G   V   K   F   I   L   G   R   E   G   S   E   P   K   240

ATC CAG CGC ATG GGC GAT CGC TTT GCG GTG GAG GTC AAG GGA AGG ATT  768
TAG GTC GCG TAC CCG CTA GCG AAA CGC CAC CTC CAG TTC CCT TCC TAA  768
 I   Q   R   M   G   D   R   F   A   V   E   V   K   G   R   I   256

CAC TTC GAC CTC TAC CCC GTC ATT AGG AGA ACG ATT AAC CTC CCC ACT  816
GTG AAG CTG GAG ATG GGG CAG TAA TCC TCT TGC TAA TTG GAG GGG TGA  816
 H   F   D   L   Y   P   V   I   R   R   T   I   N   L   P   T   272

TAC ACC CTT GAG GCA GTA TAT GAA GCC ATC TTT GGA CAG CCG AAG GAG  864
ATG TGG GAA CTC CGT CAT ATA CTT CGG TAG AAA CCT GTC GGC TTC CTC  864
 Y   T   L   E   A   V   Y   E   A   I   F   G   Q   P   K   E   288

AAG GTC TAC GCT GAG GAG ATA GCG CAG GCC TGG GAA ACG GGC GAG GGA  912
TTC CAG ATG CGA CTC CTC TAT CGC GTC CGG ACC CTT TGC CCG CTC CCT  912
 K   V   Y   A   E   E   I   A   Q   A   W   E   T   G   E   G   304

TTA GAA AGG GTG GCC CGC TAC TCG ATG GAG GAC GCG AAG GTA ACC TAT  960
AAT CTT TCC CAC CGG GCG ATG AGC TAC CTC CTG CGC TTC CAT TGG ATA  960
 L   E   R   V   A   R   Y   S   M   E   D   A   K   V   T   Y   320
```

*FIG. 3*
*(Continued)*

```
GAA CTC GGA AAA GAG TTC TTC CCT ATG GAA GCC CAG CTC TCG CGC CTC   1008
CTT GAG CCT TTT CTC AAG AAG GGA TAC CTT CGG GTC GAG AGC GCG GAG   1008
 E   L   G   K   E   F   F   P   M   E   A   Q   L   S   R   L    336

GTA GGC CAG AGC CTC TGG GAT GTA TCT CGC TCG AGT ACC GGA AAC CTC   1056
CAT CCG GTC TCG GAG ACC CTA CAT AGA GCG AGC TCA TGG CCT TTG GAG   1056
 V   G   Q   S   L   W   D   V   S   R   S   S   T   G   N   L    352

GTC GAG TGG TTT TTG CTG AGG AAG GCC TAC GAG AGG AAT GAA CTT GCA   1104
CAG CTC ACC AAA AAC GAC TCC TTC CGG ATG CTC TCC TTA CTT GAA CGT   1104
 V   E   W   F   L   L   R   K   A   Y   E   R   N   E   L   A    368

CCA AAC AAG CCG GAC GAG AGG GAG CTG GCA AGA AGA AGG GAG AGC TAC   1152
GGT TTG TTC GGC CTG CTC TCC CTC GAC CGT TCT TCT TCC CTC TCG ATG   1152
 P   N   K   P   D   E   R   E   L   A   R   R   R   E   S   Y    384

GCG GGT GGA TAC GTC AAG GAG CCC GAA AGG GGA CTG TGG GAG AAC ATC   1200
CGC CCA CCT ATG CAG TTC CTC GGG CTT TCC CCT GAC ACC CTC TTG TAG   1200
 A   G   G   Y   V   K   E   P   E   R   G   L   W   E   N   I    400

GTG TAT CTG GAC TTC CGC TCC CTG TAT CCT TCG ATA ATA ATC ACC CAT   1248
CAC ATA GAC CTG AAG GCG AGG GAC ATA GGA AGC TAT TAT TAG TGG GTA   1248
 V   Y   L   D   F   R   S   L   Y   P   S   I   I   I   T   H    416

AAC GTC TCC CCT GAT ACA CTC AAC AGG GAG GGT TGT GAG GAG TAC GAC   1296
TTG CAG AGG GGA CTA TGT GAG TTG TCC CTC CCA ACA CTC CTC ATG CTG   1296
 N   V   S   P   D   T   L   N   R   E   G   C   E   E   Y   D    432
```

FIG. 3
(Continued)

```
GTG GCT CCT CAG GTA GGC CAT AAG TTC TGC AAG GAC TTC CCC GGC TTC    1344
CAC CGA GGA GTC CAT CCG GTA TTC AAG ACG TTC CTG AAG GGG CCG AAG    1344
 V   A   P   Q   V   G   H   K   F   C   K   D   F   P   G   F     448

ATC CCA AGC CTC CTC GGA GAC CTC TTG GAG GAG AGA CAG AAG GTA AAG    1392
TAG GGT TCG GAG GAG CCT CTG GAG AAC CTC CTC TCT GTC TTC CAT TTC    1392
 I   P   S   L   L   G   D   L   L   E   E   R   Q   K   V   K     464

AAG AAG ATG AAG GCC ACT ATA GAC CCA ATC GAG AAG AAA CTC CTC GAT    1440
TTC TTC TAC TTC CGG TGA TAT CTG GGT TAG CTC TTC TTT GAG GAG CTA    1440
 K   K   M   K   A   T   I   D   P   I   E   K   K   L   L   D     480

TAC AGG CAA CGA GCA ATC AAA ATC CTT GCT AAT AGC TTC TAC GGT TAC    1488
ATG TCC GTT GCT CGT TAG TTT TAG GAA CGA TTA TCG AAG ATG CCA ATG    1488
 Y   R   Q   R   A   I   K   I   L   A   N   S   F   Y   G   Y     496

TAC GGC TAT ACA AAG GCC CGC TGG TAC TAC AAG GAG TGC GCC GAG AGC    1536
ATG CCG ATA TGT TTC CGG GCG ACC ATG ATG TTC CTC ACG CGG CTC TCG    1536
 Y   G   Y   T   K   A   R   W   Y   Y   K   E   C   A   E   S     512

GTT ACC GGT TGG GGC AGG GAG TAC ATC GAG ACC ACG ATA AGG GAA ATA    1584
CAA TGG CCA ACC CCG TCC CTC ATG TAG CTC TGG TGC TAT TCC CTT TAT    1584
 V   T   G   W   G   R   E   Y   I   E   T   T   I   R   E   I     528

GAG GAG AAA TTT GGC TTT AAA GTC CTC TAC GCG GAC ACA GAT GGA TTT    1632
CTC CTC TTT AAA CCG AAA TTT CAG GAG ATG CGC CTG TGT CTA CCT AAA    1632
 E   E   K   F   G   F   K   V   L   Y   A   D   T   D   G   F     544

TTC GCA ACA ATA CCT GGA GCG GAC GCC GAA ACC GTC AAA AAG AAG GCA    1680
AAG CGT TGT TAT GGA CCT CGC CTG CGG CTT TGG CAG TTT TTC TTC CGT    1680
 F   A   T   I   P   G   A   D   A   E   T   V   K   K   K   A     560
```

*FIG. 3*
*(Continued)*

```
AAG GAG TTC CTG GAC TAC ATC AAC GCC AAA CTG CCC GGC CTG CTC GAA   1728
TTC CTC AAG GAC CTG ATG TAG TTG CGG TTT GAC GGG CCG GAC GAG CTT   1728
 K   E   F   L   D   Y   I   N   A   K   L   P   G   L   L   E    576

CTC GAA TAC GAG GGC TTC TAC AAG CGC GGC TTC TTC GTG ACG AAG AAG   1776
GAG CTT ATG CTC CCG AAG ATG TTC GCG CCG AAG AAG CAC TGC TTC TTC   1776
 L   E   Y   E   G   F   Y   K   R   G   F   F   V   T   K   K    592

AAG TAC GCG GTT ATA GAC GAG GAG GAC AAG ATA ACG ACG CGC GGG CTT   1824
TTC ATG CGC CAA TAT CTG CTC CTC CTG TTC TAT TGC TGC GCG CCC GAA   1824
 K   Y   A   V   I   D   E   E   D   K   I   T   T   R   G   L    608

GAA ATA GTT AGG CGT GAC TGG AGC GAG ATA GCG AAG GAG ACG CAG GCG   1872
CTT TAT CAA TCC GCA CTG ACC TCG CTC TAT CGC TTC CTC TGC GTC CGC   1872
 E   I   V   R   R   D   W   S   E   I   A   K   E   T   Q   A    624

AGG GTT CTT GAG GCG ATA CTA AAG CAC GGT GAC GTT GAA GAA GCG GTA   1920
TCC CAA GAA CTC CGC TAT GAT TTC GTG CCA CTG CAA CTT CTT CGC CAT   1920
 R   V   L   E   A   I   L   K   H   G   D   V   E   E   A   V    640

AGG ATT GTC AAA GAG GTT ACG GAG AAG CTG AGC AAG TAC GAG GTT CCA   1968
TCC TAA CAG TTT CTC CAA TGC CTC TTC GAC TCG TTC ATG CTC CAA GGT   1968
 R   I   V   K   E   V   T   E   K   L   S   K   Y   E   V   P    656

CCG GAG AAG CTG GTC ATC TAC GAG CAG ATA ACC CGC GAC CTG AAG GAC   2016
GGC CTC TTC GAC CAG TAG ATG CTC GTC TAT TGG GCG CTG GAC TTC CTG   2016
 P   E   K   L   V   I   Y   E   Q   I   T   R   D   L   K   D    672
```

FIG. 3
*(Continued)*

```
TAC AAG GCC ACC GGG CCG CAT GTG GCT GTT GCA AAA CGC CTC GCC GCA   2064
ATG TTC CGG TGG CCC GGC GTA CAC CGA CAA CGT TTT GCG GAG CGG CGT   2064
 Y   K   A   T   G   P   H   V   A   V   A   K   R   L   A   A    688

AGG GGG ATA AAA ATC CGG CCC GGA ACG TCA ATA AGC TAC ATC GTG CTC   2112
TCC CCC TAT TTT TAG GCC GGG CCT TGC AGT TAT TCG ATG TAG CAC GAG   2112
 R   G   I   K   I   R   P   G   T   V   I   S   Y   I   V   L    704

AAA GGC TCG GGA AGG ATT GGG GAC AGG GCT ATA CCC TTT GAC GAA TTT   2160
TTT CCG AGC CCT TCC TAA CCC CTG TCC CGA TAT GGG AAA CTG CTT AAA   2160
 K   G   S   G   R   I   G   D   R   A   I   P   F   D   E   F    720

GAC CCG GCA AAG CAC AAG TAC GAT GCA GAA TAC TAC ATC GAG AAC CAG   2208
CTG GGC CGT TTC GTG TTC ATG CTA CGT CTT ATG ATG TAG CTC TTG GTC   2208
 D   P   A   K   H   K   Y   D   A   E   Y   Y   I   E   N   Q    736

GTT CTT CCA GCT GTG GAG AGG ATT CTG AGG GCC TTT GGT TAC CGT AAA   2256
CAA GAA GGT CGA CAC CTC TCC TAA GAC TCC CGG AAA CCA ATG GCA TTT   2256
 V   L   P   A   V   E   R   I   L   R   A   F   G   Y   R   K    752

GAA GAT TTA AGG TAT CAG AAA ACG CGG CAG GTT GGC TTG GGG GCG TGG   2304
CTT CTA AAT TCC ATA GTC TTT TGC GCC GTC CAA CCG AAC CCC CGC ACC   2304
 E   D   L   R   Y   Q   K   T   R   Q   V   G   L   G   A   W    768

CTA AAA CCT AAG ACA TGA                                            2322
GAT TTT GGA TTC TGT ACT                                            2322
 L   K   P   K   T   *                                              773
```

*FIG. 3*
*(Continued)*

THERMOSTABLE NUCLEIC ACID POLYMERASE FROM *THERMOCOCCUS GORGONARIUS*

CROSS-REFERENCES TO RELATED APPLICATIONS

The present patent application is a divisional application of U.S. patent application Ser. No. 09/269,860, filed Apr. 1, 1999, now U.S. Pat. No. 7,425,423 which is a US national phase of PCT/EP97/05393 (later published as WO 98/14590), filed Oct. 1, 1997, which claims priority to European Patent Application Nos. 96115874.8, filed Oct. 3, 1996 and 97100584.8, filed Jan. 16, 1997, each of which is incorporated by reference.

SUMMARY OF THE INVENTION

The present invention relates to an extremely thermostable enzyme. More specifically, it relates to a thermostable DNA polymerase obtainable from *Thermococcus gorgonarius*.

DNA polymerases are a family of enzymes which are in particular involved in DNA replication and repair. Extensive research has been conducted on the isolation of DNA polymerases from mesophilic microorganisms such as *E. coli* (see, e.g., Bessman et al., *J. Biol. Chem.*, 223:171-177 (1957), and Buttin and Kornberg, *J. Biol. Chem.*, 241:5419-5427 (1966)).

Research has also been conducted on the isolation and purification of DNA polymerases from thermophiles, such as *Thermus aquaticus* (Chien, A. et al., *J. Bacteriol.*, 127:1550-1557 (1976)). Further, the isolation and purification of a DNA polymerase with a temperature optimum of 80° C. from *Thermus aquaticus* YT1 strain has been described (EP 0 258 017 and U.S. Pat. No. 4,889,819).

Research has indicated that while the Taq DNA polymerase has a 5'-3' polymerase-dependent exonuclease function, the Taq DNA polymerase does not possess a 3'-5' proofreading exonuclease function (Lawyer, F. C. et al., *J. Biol. Chem.*, 264:6427-6437 (1989); Bernad, A. et al., *Cell*, 59:219 (1989)). As a result, Taq DNA polymerase is prone to base incorporation errors, making its use in certain applications undesirable. For example, attempting to clone an amplified gene is problematic since any one copy of the gene may contain an error due to a random misincorporation event. Depending on where in the PCR cycle that error occurs (e.g., in an early replication cycle), the entire DNA amplified could contain the erroneously incorporated base, thus, giving rise to a mutated gene product. Furthermore, research has indicated that Taq DNA polymerase has a thermal stability of not more than several minutes at 100° C.

The 3'-5' exonuclease activity is generally considered to be desirable, because misincorporated or unmatched bases of the synthesized nucleic acid sequence are eliminated by this activity. Therefore, the fidelity of PCR utilizing a polymerase with 3'-5' exonuclease activity is increased. Such an enzyme is, e.g., the DNA polymerase from *Pyrococcus furiosus* (Lundberg et al., *Gene*, 108:1-6 (1991)).

Other more recent investigation focuses on the isolation and purification of DNA polymerases from archaebacteria such as *Thermococcus* sp. (EP 0 455 430), in particular a purified DNA polymerase obtainable from *Thermococcus litoralis* is described. Also the recombinant preparation and the gene encoding for this enzyme is known in the art (EP 0 547 920).

In EP 0 455 430 is also described a DNA polymerase from *Pyrococcus* sp. and the gene thereof which also contains introns to be removed for expression of the functional enzyme in *E. coli*.

In EP 0 701 000 A and in *Proc. Natl Acad. Sci. USA*, Vol. 93, No. 11, pp. 5281-5285 (1996), a thermostable DNA polymerase 9° N7 is described which exhibits a very strong 3'-5'-exonuclease activity. However, it has been observed that the 9° N7 polymerase exhibits a tendency to degrade single stranded DNA (primer). Therefore, the exonuclease activity has been modulated and a mutant 9° Nm polymerase has been obtained which is more useful for a number of applications as the native enzyme. However, when using a 9° Nm polymerase for PCR (see FIG. 6), a primer-template independent DNA-synthesis seems to occur (as can be deducted from the observed highmolecular smear in the gel (FIG. 6)) instead of the occurrence of defined PCR products when using, e.g., Taq-Polymerase. Therefore, neither the native nor the exonuclease modulated 9° N7 polymerase can be successfully used in PCR.

In WO 92/03556, a thermostable DNA polymerase obtainable from the eubacterium *Thermotoga maritima* is described which also exhibits proofreading activity. However, in comparison to other DNA polymerases, e.g., Pfu polymerase or Tgo polymerase, the Tma polymermase exhibits a relatively low fidelity (Flaman, J. M. et al., *Nucl. Acids. Res.*, 22:3259-3260 (1994); Cline, J. et al., *Nucl. Acids. Res.*, 24:3546-3551 (1996)).

The DNA polymerase obtainable from *Pyrococcus furiosis* (Pfu) is described in WO 92/09689 and exhibits a relatively high fidelity.

Accordingly, there is a desire in the art to obtain and produce a purified, highly thermostable DNA polymerase with 3'-5' proofreading exonuclease activity which exhibits a high fidelity and is suitable to improve the PCR process.

The present invention meets this need by providing a DNA polymerase from *Thermococcus gorgonarius* (Tgo), together with the related DNA and amino acid sequence information, recombinant expression vector and a purification protocol for said DNA polymerase. The DNA polymerase according to the present invention exhibits more than a two fold greater replication fidelity than known DNA polymerases, e.g., obtainable from *Pyrococcus furiosus*. A further advantage is that the 3'-5'exonuclease activity found in *T. gorgonarius* polymerase can also decrease non-specific background amplification in PCR by degrading defrayed ends of primers bound to unspecific sequences thereby destabilizing the binding of the primer because of decreasing the length of the helix. Tgo polymerase is thus unexpectedly superior to known DNA polymerases in amplification protocols requiring high fidelity DNA synthesis (see FIGS. 8-10). Another advantageous property of the DNA polymerase of *Thermococcus gorgonarius* is the fact, that the gene does not contain intervening sequences which would have to be removed to accomplish expression in *E. coli*.

The thermostable DNA polymerase enzyme obtainable from *T. gorgonarius* catalyzes the template directed polymerization of DNA, has an apparent molecular weight of about 92,000-96,000 daltons and retains 90% of its activity after incubation for two hours at 95° C. in the presence of a stabilizer like a non-ionic detergent as, e.g., 0.01% THESIT™ (Dodecylpoly(ethylenglycolether)$_n$) or 0.01% NONIDET P40™ (Ethylphenolpoly(ethylenglycolether)$_n$).

Moreover, DNA encoding the 92,000-96,000 daltons thermostable DNA polymerase obtainable from *Thermococcus gorgonarius* has been isolated and which allows to obtain the thermostable enzyme of the present invention by expression in *E. coli*. The DNA sequence of the DNA polymerase obtainable from *Thermococcus gorgonarius* is shown in SEQ ID NO:6. The recombinant *Thermococcus gorgonarius* DNA polymerase also possesses 3'-5' exonuclease (proofreading) activity. Furthermore the gene encoding DNA polymerase from *Thermococcus gorgonarius* does not contain intervening sequences.

*Thermococcus gorgonarius* was isolated from E. A. Bonch-Osmolovskaya and V. A. Svetlichny, Institute of Microbiology, Russian Academy of Sciences, Moscow, Russia. *Thermococcus gorgonarius* is a new strain, isolated from a thermal vent in New Zealand. This strain does not show DNA-DNA homology with *T. celer, T. litoralis* or *T. stetteri* (E. A. Bonch-Osmolovskaya, unpublished results).

The preferred thermostable enzyme herein is a DNA polymerase obtainable from *Thermococcus gorgonarius* DSM 8976 (deposited on the Deutsche Sammlung von Mikroorganismen and Zellkulturen GmbH, Mascheroder Weg 1b, D-38124 Braunschweig). This organism is an extremely thermophilic, sulfur metabolizing, archaebacterium, with a growth range between 55° C. and 98° C.

A preferred method for isolation and purification of the enzyme is accomplished—after all growth—using the multistep process as follows:

First, the frozen cells are thawed, suspended in a suitable buffer such as buffer A (40 mM Tris-HCl buffer, pH 7.4; 0.1 mM EDTA, 7 mM 2-mercaptoethanol; 1 mM Pefabloc SC™ (4-(2-Aminoethyl)-benzolsulfonylfluorid)), disrupted by high pressure at 1.200 bar. KCl was added to the extract to a final concentration of 400 mM and the solution cleared by centrifugation. The supernatant is then passed through a Heparin Sepharose Cl 6B column (Pharmacia), which has a strong affinity for nucleic acid binding proteins. The nucleic acids present in the supernatant solution of *Thermococcus gorgonarius* and many of the other proteins pass through the column and are removed by washing the column with two column volumes of buffer A. After washing, the enzyme is eluted with a linear gradient from 0 to 1 M NaCl in buffer A. The peak DNA polymerase activity is dialyzed and applied to a DEAE Sephacel column (Pharmacia). The column is washed with buffer A and the enzyme activity eluted with a linear gradient from 0 to 1 M NaCl in buffer A. The peak DNA polymerase activity is dialyzed and applied to a Cellulose Phosphate column (Whatman). The enzyme is again eluted with a linear gradient such as 0 to 1 M NaCl in buffer A. The enzyme is about 40% pure at this stage.

The apparent molecular weight of the DNA polymerase obtainable from *Thermococcus gorgonarius* is between about 92,000 to 96,000 daltons when compared with DNA polymerases of known molecular weight, such as *E. coli* DNA polymerase I and *Thermus thermophilus* DNA polymerase. It should be understood, however, that as a protein from an extreme thermophile, *Thermococcus gorgonarius* DNA polymerase may migrate during electrophoresis at an aberrant relative molecular weight due to failure to completely denature or other intrinsic properties. The exact molecular weight of the thermostable enzyme of the present invention may be determined from the coding sequence of the *Thermococcus gorgonarius* DNA polymerase gene. The molecular weight of the DNA polymerise may be determined by any technique, for example, by in situ analysis after separation by SDS-polyacrylamide gel electrophoresis (SDS-PAGE) as described in Spanos, A. and Hübscher, U., *Methods in Enzymology*, 91:263-277 (1983).

Polymerase activity is either measured by the incorporation of radioactively labeled deoxynucleotides into DNAse-treated, or activated DNA, following subsequent separation of the unincorporated deoxynucleotides from the DNA substrate. Polymerase activity is proportional to the amount of radioactivity in the acid-insoluble fraction comprising the DNA, as described by Lehman, I. R. et al., *J. Biol. Chem.*, 233:163 (1958), or by incorporation of digoxigeninlabeled dUTP and determination of incorporated Digoxigenin-dUTP using chemoluminescence according to the method described in Höltke, H. J. et al., *Biotechniques*, 12:104-113 (1992).

The DNA polymerase of the present invention has a very high thermal stability at 95° C. It retains approximately 90 percent of its activity after incubation at 95° C. for 120 minutes in the presence of stabilizer. The thermal stability is determined by pre-incubating the enzyme at the temperature of interest in the presence of all assay components (buffer, MgCl$_2$, deoxynucleotides, activated DNA and a stabilizer like 0.01% THESIT™ and 0.01% NONIDET P40™), except the single radioactively-labeled deoxynucleotide. At predetermined time intervals, ranging from 1-120 minutes, small aliquots are removed, and assayed for polymerase activity using one of the methods described above.

The thermostable enzyme of this invention may also be produced by recombinant DNA techniques, as the gene encoding this enzyme has been cloned from *Thermococcus gorgonarius* genomic DNA. The complete coding sequence for the *Thermococcus gorgonarius* DNA polymerase can be derived from the plasmid pBTac2Tgo on an approximately 2.3 kB EcoRI/PstI restriction fragment.

The production of a recombinant form of *Thermococcus gorgonarius* DNA polymerase generally includes the following steps: DNA is isolated which codes for the active form of the polymerase. This can be accomplished, e.g., by screening of a DNA library derived from the genomic DNA of *T. gorgonarius* using the DNA sequence described in SEQ ID NO:1 as a probe. Clones containing DNA fragments of *T. gorgonarius* hybridizing to the probe are isolated and the nucleotide sequence of the plasmid inserts determined. Complete isolation of the coding region and the flanking sequences of the DNA polymerase gene can be performed by restriction fragmentation of the *T. gorgonarius* DNA with another restriction enzyme as in the first round of screening and by inverse PCR (Innis et al., *PCR Protocols*, Academic Press, Inc., 219-227 (1990)). This can be accomplished with synthesized oligonucleotide primers binding at the outer DNA sequences of the gene part but in opposite orientation, e.g., with the SEQ ID NOS:2 and 3. As template *T. gorgonarius* DNA is used which is cleaved by restriction digestion and circularized by contacting with T4 DNA ligase. To isolate the coding region of the whole polymerase gene, another PCR is performed using primers as shown in SEQ ID NOS:4 and 5 to amplify the complete DNA polymerase gene directly from genomic DNA and introducing ends compatible with the linearized expression vector.

```
SEQ ID NO: 1:
5'-ATG ATH YTN GAY ACN GAY TAY ATH AC-3'

SEQ ID NO: 2:
5'-GGC CTA CGA GAG GAA CGA ACT GGC-3'

SEQ ID NO: 3:
5'-GGC GTA GAT GTA GGG CTC-3'

SEQ ID NO: 4:
5'-GAG CTG GTC GAA TTC ATG ATC CTG GAC GCT GAC TAC
ATC ACC-3'

SEQ ID NO: 5:
5'-AGC CTG CAG TCA TGT CTT AGG TTT TAG CCA CGC-3'
```

The gene is operably linked to appropriate control sequences for expression in either prokaryotic or eukaryotic host/vector systems. The vector preferably encodes all functions required for transformation and maintenance in a suitable host, and may encode selectable markers and/or control sequences for polymerase expression. Active recombinant thermostable polymerase can be produced by transformed host cultures either continuously or after induction of expression. Active thermo stable polymerase can be recovered either from host cells or from the culture media if the protein is secreted through the cell membrane.

It is also preferable that *Thermococcus gorgonarius* thermostable polymerase expression is tightly controlled in *E. coli* during cloning and expression. Vectors useful in practicing the present invention should provide varying degrees of controlled expression of *Thermococcus gorgonarius* polymerase by providing some or all of the following control features: (1) promoters or sites of initiation of transcription, either directly adjacent to the start of the polymerase gene or as fusion proteins, (2) operators which could be used to turn gene expression on or off, (3) ribosome binding sites for improved translation, and (4) transcription or translation termination sites for improved stability. Appropriate vectors used in cloning and expression of *Thermococcus gorgonarius* polymerase include, for example, phage and plasmids. Example of phage include lambda gt11 (Promega), lambda Dash (Stratagene), lambda ZapII (Stratagene). Examples of plasmids include pBR322, pBTac2 (Boehringer Mannheim), pBluescript (Stratagene), pSP73 (Promega), pET3A (Rosenberg, A. H. et al., *Gene*, 56:125-135 (1987)) and pET11C (Studier, F. W. et al., *Methods in Enzymology*, 185:60-89 (1990)). According to the present invention the use of a plasmid has shown to be advantageously, particularly pBTac2. The Plasmid pBTac2 carrying the *Thermococcus gorgonarius* DNA polymerase gene is then designated pBTac2Tgo.

Standard protocols exist for transformation, phage infection and cell culture (Maniatis et al., *Molecular Cloning: A Laboratory Manual*, Cold Spring Harbour Laboratory Press (1982)). Of the numerous *E. coli* strains which can be used for plasmid transformation, the preferred strains include JM110 (ATCC 47013), LE392 pUBS 520 (Maniatis et al., supra; Brinkmann et al., *Gene*, 85:109-114 (1989); JM101 (ATCC No. 33876), XL1 (Stratagene), and RR1 (ATCC No. 31343), and BL21 (DL3) plysS (Studier, F. W. et al., supra). According to the present invention, the use of the *E. coli* strain LE392 pUBS 520 has shown to be advantageous. The *E. coli* strain LE392 pUBS 520 transformed with the plasmid pBTac2Tgo is then designated *E. coli* pBtac2Tgo (DSM No. 11328). *E. coli* strain XL1 Blue (Stratagene) is among the strains that can be used for lambda phage, and Y1089 can be used for lambda gt11 lysogeny. The transformed cells are preferably grown at 37° C. and expression of the cloned gene is induced with IPTG (Isopropyl-β-D-thiogalactopyranosid).

Isolation of the recombinant DNA polymerase can be performed by standard techniques. Separation and purification of the DNA polymerase from the *E. coli* extract can be performed by standard methods. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electric charge such as ion-exchange column chromatography, methods utilizing specific interaction such as affinity chromatography, methods utilizing a difference in hydrophobicity such as reversed-phase high performance liquid chromatography and methods utilizing a difference in isoelectric point such as isoelectric focusing electrophoresis.

One preferred method for isolating and purification of the recombinant enzyme is accomplished using the multi-stage process as follows.

The frozen cells are thawed and suspended in a suitable buffer such as buffer A (40 mM Tris-HCl, pH 7.5; 0.1 mM EDTA; 7 mM 2-mercaptoethanol) in the presence of Pefabloc SC in a final concentration of 1 mM, lysed by the addition of lysozyme (200 μg/ml) under stirring for 30 minutes at 4° C. Sodium deoxycholate is added to a final concentration of 0.05%. After an incubation for another 30 minutes, KCl is added to a final concentration of 0.75 M. The suspension is incubated at 72° C. for 15 minutes and centrifuged. The supernatant is adjusted to 25% saturation with $(NH_4)_2SO_4$ and then applied to a hydrophobic interaction chromatography column such as TSK Butyl Toyopearl 650C (TosoHaas). Most of the nucleic acids and unspecific proteins are in the flow through and wash of the column while the polymerase is eluting at the end of a decreasing gradient from 30% to 0% saturation of $(NH_4)_2SO_4$ in buffer A (with additional 10% glycerol). The polymerase-active fractions are pooled, dialyzed against buffer A containing 10% glycerol, adjusted to 10 mM $MgCl_2$ and applied to a high affinity column for nucleotide-binding enzymes such as Fractogel TSK AF-Blue column (Merck). The column is washed with buffer A containing 10% glycerol and the polymerase protein is eluted with a linear gradient of 0 to 3 M NaCl in buffer A (with additional 10% glycerol). The polymerase fractions are pooled and dialyzed against the storage buffer B (20 mM Tris-HCl, pH 8.0; 0.1 mM EDTA; 10 mM 2-mercaptoethanol; 50 mM $(NH_4)_2SO_4$; 50% glycerol) and stored at −20° C.

The *Thermococcus gorgonarius* DNA polymerase of the present invention may be used for any purpose in which such an enzyme is necessary or desirable. For example, in recombinant DNA technology, including second-strand cDNA synthesis in cDNA cloning and DNA sequencing (see Maniatis et al., supra).

The *Thermococcus gorgonarius* DNA polymerase of the present invention may be modified chemically or genetically—site directed or random—to inactivate the 3'-5' exonuclease function and used for any purpose in which such a modified enzyme is desirable, e.g., DNA sequencing or DNA labeling.

In addition, the *Thermococcus gorgonarius* DNA polymerase of the present invention may also be used to amplify DNA, e.g., by the procedure disclosed in EP 0 200 362, EP 0 201 184 and EP 0 693 078.

The following examples are given to illustrate embodiments of the present invention as it is presently preferred to practice. It will be understood that the examples are illustrative, and that the invention is not be considered as restricted except as indicated in the appended claims.

Figure 1:
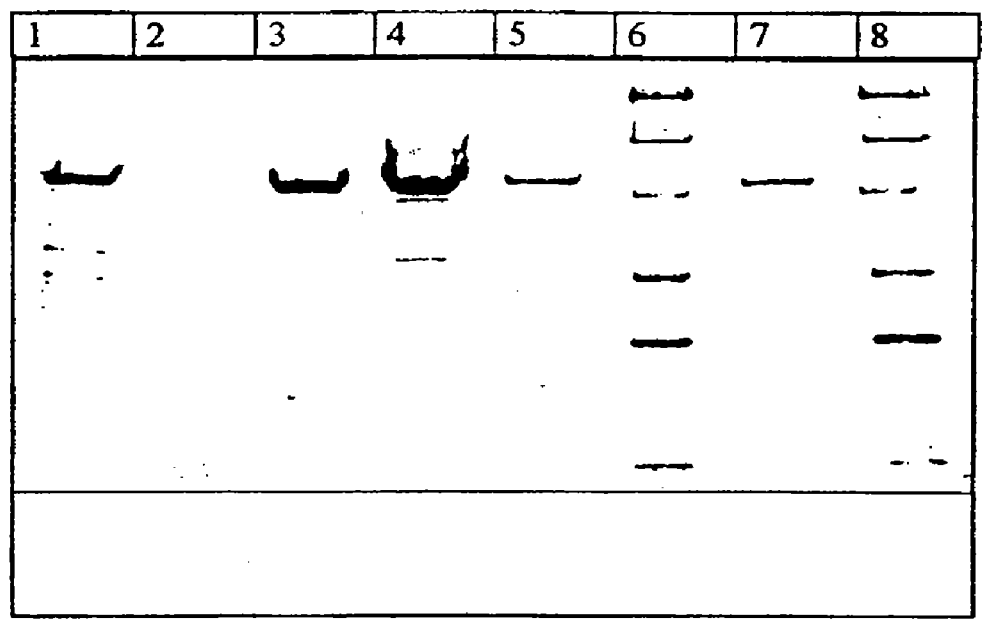
FIG. 1:
SDS polyacrylamide gel analysis of partially purified and purified recombinant DNA polymerase from *T. gorgonarius*.
Lane 1: 1 μl of crude extract.
Lane 2: 5 μl of polymerase fraction obtained after the first chromatography step (TSK Butyl Toyopearl 650C).
Lane 3: 5 μl of fraction obtained after second chromatography step (Fractogel Blue).
Lane 4: 10 μl of fraction obtained after second chromatography step (Fractogel Blue).
Lane 5: 10 units of DNA polymerase from *Thermococcus gorgonarius*.
Lane 6: Molecular weight markers.
Lane 7: 10 units of DNA polymerase from *Pyrococcus woesei*.
Lane 8: Molecular weight markers.

In situ activity analysis of native and recombinant *Thermococcus gorgonarius* DNA polymerase in comparison to Klenow fragment, Pol I of *E. coli* and *Thermus thermophilus* DNA polymerase as described in Example 1. Native and recombinant *Thermococcus gorgonarius* DNA polymerase have the same electrophoretic mobility.

FIG. 3:

DNA sequence (SEQ ID NO.:6 (top nucleic acid sequence) and the complement of SEQ ID NO:6 (bottom nucleic acid sequence)) and the deduced amino acid sequence (SEQ ID NO.:7) of the gene encoding the DNA polymerase from *Thermococcus gorgonarius*.

FIG. 4:

Determination of heat stability of *T. gorgonarius* polymerase as described in Example 5.

FIG. 5:

Analysis of 3'-5' exonuclease activity as described in Example 6.

Various amounts (units are indicated in the figure) of *T. gorgonarius* DNA polymerase were incubated with DNA fragments in the absence (−dNTPs) and presence (+dNTPs) of desoxynucleotide triphosphates. ctrl1 and 2: Control reactions without DNA polymerase.

The 3'-5'exonuclease activity is dependent on the presence or absence of dNTPs.

FIG. 6:

Comparison of various thermostable DNA polymerases (Vent exo-, 9° Nm, Taq) with respect to the incorporation of Cy5-dUTP. The reaction mixtures contained 2 mM $MgCl_2$, 30 nM of each primer, 1 ng DNA and 200 µM deoxynucleotide. Buffer conditions were used as recommended by the supplier of the enzymes. Plasmid DNA has been used in which the β-Actin-gene of the mouse has been inserted. TTP has been partly replaced by Cy5-dUTP. The reaction mixture contained Cy5-dUTP:TTP in the following ratios: 65:35 (lane 1), 50:50 (lane 2), 35:65 (lane 3), 15:85 (lane 4). As a control the above described reaction has been performed without modified nucleosidetriphosphates (lane 5).

FIG. 7:

Use of TgO-polymerase in PCR, applying different amounts of polymerase as well as different $MgCl_2$ concentrations.

FIG. 8:

Use of TgO-polymerase in PCR, applying different amounts of TgO polymerase; comparison of TgO and Pfu polymerase.

FIG. 9:

Amplification of λ-DNA; Comparison of TgO and Pfu polymerise.

FIG. 10:

Comparison of TgO and Pfu polymerase; investigation of the influence of the KCl concentration on the PCR; 2.5 U polymerase has been used in every assay.

EXAMPLES

Example 1

Purification of a Thermostable DNA Polymerase from *Thermococcus gorgonarius*

*Thermococcus gorgonarius* (DSM 8976) was grown in the medium which was prepared as follows: A mineral solution containing KCl, 325 mg/l; $MgCl_2$ $2H_2O$, 2.75 mg/l; $MgSO_4$ $7H_2O$, 3.45 mg/l; $NH_4Cl$, 0.25 mg/l; $CaCl_2$ $2H_2O$, 0.15 mg/l; $KH_2PO_4$, 0.15 mg/l; NaCl, 18 g/l; $NaHCO_3$, 1 g/l; trace elements, 4 ml/l (Balch et al., *Microbiol. Rev.*, 43:260 (1979)), vitamins, 4 ml/l (Balch et al., supra); Rezazurin, 1 mg/l; 0.4 ml/l of a 0.2% solution of $Fe(NH_2)_2(SO_4)_2$ $7H_2O$ was boiled and cooled. The following components were added to the final concentrations as indicated: Peptone, 5 g/l; yeast extract, 1 g/l; $Na_2S.9H_2O$, 250 mg/l and cystein-HCl, 250 mg/l, the pH was adjusted to 6.2-6.4. The incubation temperature was 88° C. The cells were cooled to room temperature, collected by centrifugation and stored at −70° C. 6 g of cells were suspended in 12 ml of buffer A (40 mM Tris-HCl, pH 7.5; 0.1 mM EDTA; 7 mM 2-mercaptoethanol) containing 1 mM Pefabloc SCTM and disrupted by pressure at 1200 bar. KCl was added to a final concentration of 400 mM, dissolved and the solution was centrifuged at 48,200×g for 30 minutes at 4° C. The supernatant was passed through a 31 ml Heparin Sepharose Cl 6B column (Pharmacia). The column was then washed with 62 ml of buffer B (buffer A containing 10% glycerol). The column was eluted with a 310 ml linear gradient from 0 to 1.0 M NaCl in buffer B. The DNA polymerase eluted between 30 and 45 mS/cm. The fractions containing DNA polymerase activity were pooled and dialyzed twice against 600 ml buffer b, respectively, and applied to a 18 ml DEAE Sephacel column (Pharmacia). The column was washed with two column volumes of buffer b, and eluted with a 160 ml linear gradient of 0 to 0.9 M NaCl in buffer b. The polymerase activity eluted between 4 and 14 mS/cm. Fractions were pooled, dialyzed twice against buffer B (200 ml each time), and applied to a 4 ml Cellulose Phosphate P11 column (Whatman). The column was washed with 8 ml of buffer B and the activity eluted with a 40 ml linear gradient of 0 to 1 M NaCl. The active fractions which eluted between 13 and 32 mS/cm were pooled, dialyzed against buffer B containing $(NH_4)_2SO_4$ to 25% saturation and applied to a 4 ml TSK Butyl Toyopearl 650C column (TosoHaas). The column was washed with 8 ml 25% $(NH_4)_2SO_4$-saturated buffer B and eluted with 40 ml of a decreasing gradient of 25% to 0% $(NH_4)_2SO_4$-saturated buffer b. The polymerase eluted between 74 and 31 mS/cm, the pool was dialyzed against buffer B and applied to a 4 ml Fractogel TSK AF-Orange column (Merck). The column was washed with 8 ml of buffer B and eluted with a 80 ml linear gradient of 0 to 2.0 M NaCl. The active fractions (between 76 and 104 mS/cm) were pooled and dialyzed against storage buffer C (20 mM Tris-HCl, pH 8.0; 0.1 mM EDTA; 10 mM 2-mercaptoethanol; 50 mM $(NH_4)_2SO_4$; 50% glycerol) and stored at −20° C. At this step the DNA polymerase was approximately 40% pure.

Figure 2:
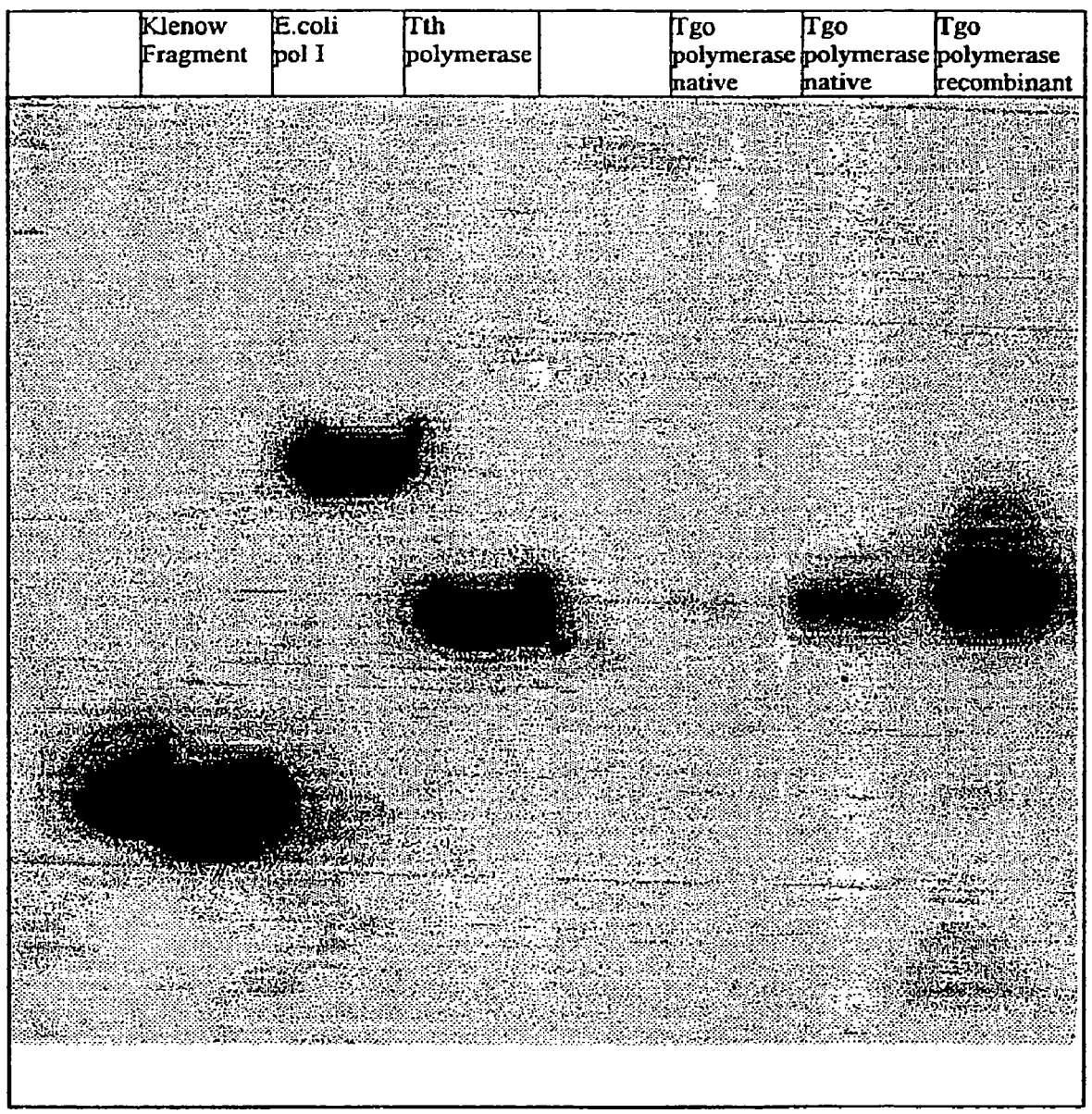
FIG. 2.

The molecular weight of the isolated DNA polymerase was determined by "activity gel analysis" according to a modified version of the method described by Spanos, A. and Hubscher, U., supra. The DNA polymerase sample was separated on a SDS polyacrylamide gel containing activated calf thymus DNA. The polymerase was renaturated in the gel in 50 mM Tris-HCl, pH 8.8; 1 mM EDTA; 3 mM 2-mercaptoethanol; 50 mM KCl; 5% glycerol. Labeling of the DNA with Dig-dUTP (Boehringer Mannheim) was performed in 10 ml of the following buffer: 50 mM Tris-HCl, pH 8.8; 7 mM $MgCl_2$; 3 mM 2-mercaptoethanol; 100 mM KCl; 12 µM dGTP; 12 µM dCTP; 12 µM dATP; 6 µM dTTP; 6 µM Dig-dUTP. The gel was first incubated under shaking at room temperature (30 minutes) and then slowly warmed up to 72° C. by temperature increments of 5° C. At each temperature interval DNA synthesis is allowed to proceed for 30 minutes, in order to detect also polymerase activity of mesophile control polymerases. Then the gel was washed and the DNA was blotted on a nylon membrane (Boehringer Mannheim), UV crosslinked. The digoxygenin-labeled DNA was detected using the protocol described in the "Boehringer Mannheim's Dig System User's Guide for Filter Hybridization". As molecular weight markers *E. coli* DNA polymerase I, *Thermus thermophilus* DNA polymerase and Klenow fragment were analyzed on the same gel. The DNA polymerase isolated from *Thermococcus gorgonarius* has an apparent molecular weight in the range of 92,000 to 96,000 daltons as shown in FIG. 2.

Example 2

Cloning of the *T. gorgonarius* DNA Polymerase

1. DNA from *T. gorgonarius* was isolated and purified by the method described in Lawyer, F. C. et al., *J. Biol. Chem.*, 264:6427-6437 (1989).
2. The DNA was restricted with BamHI, separated on an low melting point agarose gel, denatured and blotted onto a nylon membrane. The blot was probed with a Digoxigenin labeled oligonucleotide of the sequence shown in SEQ ID NO:1. A signal could be detected and the region corresponding to the hybridization signal was cut out of the gel. The gel piece was melted and the DNA isolated by ethanol precipitation.
3. The DNA fragments isolated were ligated into a plasmid vector, hybridized with SEQ ID. NO:1. The plasmid DNA from positive clones were isolated and the nucleic acid sequences of the insert determined. The DNA sequences obtained were then compared with sequences of DNA polymerase genes published in Braithwaite, D. K. and Ito, J., *Nucl. Acids Res.*, 21:787-802 (1993).
4. From the sequence of one of the cloned fragments which showed a high degree of homology to the B type DNA polymerases described in the publication of Braithwaite et al., supra, the primers SEQ ID NOS:2 and 3 were designed. These primers bind close to the ends of the cloned DNA fragment in opposite orientations to allow amplification of the flanking genomic sequences in circularized template DNA.
5. With these primers "inverse PCR" was performed according of the method of Innis, M. A., supra, with the DNA from step 1 which was cleaved with EcoRI and circularized with T4 DNA ligase. With this technique two fragments were generated and the sequences determined. An open reading frame could be identified. The deduced amino acid sequence showed strong homologies to known DNA polymerases of the pol B type.
6. From the sequence of the DNA fragment identified in step 5, new primers were designed, the sequences are shown in SEQ ID NOS:4 and 5, which were complementary to the start and the end of the reading frame. The primers contained additional non-complementary 5' sequences with restriction sites to introduce clonable ends into the PCR product in such an orientation that the product would be under transcriptional and translational control of the promoter.
7. The PCR product was cleaved with EcoRI and PstI, purified and ligated into the vector pBTac2. This clone, expressing the DNA polymerase from *Thermococcus gorgonarius* was designated pBTac2Tgo.

SEQ ID NO: 1:
5'-ATG ATH YTN GAY ACN GAY TAY ATH AC-3'

SEQ ID NO: 2:
5'-GGC CTA CGA GAG GAA CGA ACT GGC-3'

-continued

SEQ ID NO: 3:
5'-GGC GTA GAT GTA GGG CTC-3'

SEQ ID NO: 4:
5'-GAG CTG GTC GAA TTC ATG ATC CTG GAC GCT GAC TAC ATC ACC-3'

SEQ ID NO: 5:
5'-AGC CTG CAG TCA TGT CTT AGG TTT TAG CCA CGC-3'

Example 3

Expression of Recombinant *T. gorgonarius* DNA

The vector from example 2 was transformed into *E. coli* strain LE 392 pUBS 520, cultivated in a fermentor in a rich medium containing the appropriate antibiotic. Induction was performed at an optical density of 1.25 A540 with 0.5 mM IPTG. The DNA polymerase from *T. gorgonarius* may also be cloned and expressed by other methods.

Cells are harvested at an optical density of 5.4 $A_{540}$ by centrifugation and frozen until needed or lyzed by treatment with lysozyme to produce a crude cell extract containing the *T. gorgonarius* DNA polymerase activity.

The crude extract containing the *T. gorgonarius* DNA polymerase activity is purified by the method described in Example 1, or by other purification techniques such as affinity-chromatography, ion-exchange-chromatography or hydrophobic-interaction-chromatography.

Example 4

Purification of Recombinant *T. gorgonarius* DNA Polymerase

*E. coli* (LE392 pUBS520) pBtac2Tgo (DSM No. 11328) was grown in a 10l fermentor in media containing 20 g/liter tryptone, 10 g/liter yeast extract, 5 g/liter NaCl and 100 mg/liter ampicilline at 37° C. and induced with 0.5 mM IPTG at mid-exponential growth phase and incubated an additional 4 hours. About 45 g of cells were harvested by centrifugation and stored at −70° C.

2 g of cells were thawed and suspended at room temperature in 4 ml of buffer A (40 mM Tris-HCl, pH 7.5; 0.1 mM EDTA; 7 mM 2-mercaptoethanol; 1 mM Pefabloc SC). 1.2 mg of lysozyme were added and the cells were lyzed under stirring for 30 minutes at 4° C. 4.56 mg sodium deoxycholate were added and the suspension incubated for 10 minutes at room temperature followed by 20 minutes at 0° C. The crude extract was adjusted to 750 mM KCl, heated for 15 minutes at 72° C. and centrifuged for removal of denatured protein.

The supernatant was adjusted to 25% saturation with $(NH_4)_2SO_4$ and applied to a TSK Butyl Toyopearl 650C column (1.5×10 cm; 17.7 ml bed volume) equilibrated with buffer B (buffer A containing 10% glycerol) and 30% $(NH_4)_2SO_4$ saturation. The column was washed with 70 ml of buffer B and the polymerase was eluted with a 177 ml linear gradient of buffer B containing 30% to 0% $(NH_4)_2SO_4$ saturation and 0 to 0.2% THESIT™ (v/v).

The column fractions were assayed for DNA polymerase activity. DNA polymerase activity was measured by incorporation of digoxigenin labeled dUTP into the newly synthesized DNA and detection and quantification of the incorporated digoxigenin essentially as described below. The reaction is performed in a reaction volume of 50 µl containing 50 mM Tris-HCl, pH 8.5; 15 mM $(NH_4)_2SO_4$; 7 mM $MgCl_2$; 10 mM 2-mercaptoethanol; 100 µM of dATP, dGTP, dCTP, dTTP, respectively; 200 µg/ml BSA; 12 µg of DNAse activated DNA from calf thymus and 0.036 µM digoxigenin-dUTP and 1 or 2 Al of diluted (0.05 U to 0.01 U) DNA polymerase from *T. gorgonarius*. The samples are incubated for 30 minutes at 72° C., the reaction is stopped by addition of 2 µl of 0.5 M EDTA, and the tubes placed on ice. After addition of 8 Al of 5 M NaCl and 150 µl of Ethanol (pre-cooled to −20° C.) the DNA is precipitated by incubation for 15 minutes on ice and pelleted by centrifugation for 10 minutes at 13,000 rpm and 4° C. The pellet is washed with 100 µl of 70% Ethanol (pre-cooled to −20° C.) and 0.2 M NaCl, centrifuged again and dried under vacuum. The pellets are dissolved in 50 µl Tris/EDTA (10 mM/0.1 mM; pH 7.5). 5 µl of the sample are spotted into a well of a nylon membrane bottomed white microwell plate (Pall Filtrationstechnik GmbH, Dreieich, FRG, product no: SM045BWP). The DNA is fixed to the membrane by baking for 10 minutes at 70° C. The DNA-loaded wells are filled with 100 µl of 0.45 µm filtrated 1% blocking solution (maleic acid, 100 mM; NaCl, 150 mM; casein, 1% (w/v); pH 7.5). All following incubation steps are done at room temperature. After incubation for 2 minutes the solution is sucked through the membrane with a suitable vacuum manifold at −0.4 bar. After repeating the washing step once the wells are filled with 100 µl of a 1:10,000-dilution of Anti-digoxigenin-AP Fab fragments (Boehringer Mannheim, FRG, No: 1 093 274) diluted in the blocking solution described above. After incubation for 2 minutes and sucking the solution through the membrane, this step is repeated once. The wells are washed twice under vacuum with 200 µl washing-buffer 1 (maleic-acid, 100 mM; NaCl, 150 mM; TWEEN™ 20, 0.3% (v/v); pH 7.5). After washing for another two times under vacuum with 200 µl washing-buffer 2 (Tris-HCl, 10 mM; NaCl, 100 mM; $MgCl_2$, 50 mM; pH 9.5) the wells are incubated for 5 minutes with 50 µl of CSPD™ (Boehringer Mannheim, No: 1 655 884), diluted 1:100 in washing buffer 2 which serves as a chemiluminescent substrate for the subsequent alkaline phosphatase reaction.

The solution is sucked through the membrane and after 10 minutes incubation the RLU/s (Relative Light Unit per second) are detected in a Lummometer, e.g., MicroLumat LB 96 P (EG&G Berthold, Wilbad, FRG).

In order to correlate the relative light units to the polymerase units as defined commonly, a standard curve was prepared using a serial dilution of Taq DNA polymerase as a standard enzyme. The Taq polymerase was assayed in the buffer recommended by the supplier. The linear range of the standard curve was used to determine the relative activity of the *T. gorgonarius* DNA polymerase preparations.

The active fractions were pooled, dialyzed twice against 500 ml buffer B and applied to a Fractogel TSK AF-Blue column (1×10; 7.8 ml bed volume) equilibrated with buffer B. After washing with 15 ml buffer B b the column was eluted with a linear gradient of 156 ml from 0 to 3 M NaCl in buffer B supplemented with 0.05% THESIT™. The active fractions were pooled and dialyzed against the storage buffer C (20 mM Tris-HCl, pH 8.2; 10 mM 2-mercaptoethanol; 0.1 mM EDTA; 50 mM $(NH_4)_2SO_4$; 50% glycerol). After adding of 0.5% of NONIDET™ P40 (v/v) and 0.5% of THESIT™ (v/v) the preparation was stored at −20° C.

Characterization of the Recombinant DNA Polymerase from *Thermococcus gorgonarius*

Recombinant and native *T. gorgonarius* DNA polymerase had the same apparent molecular weight when electrophoresed in 8-25% SDS-PAGE gradient gels. Recombinant *T. gorgonarius* polymerase maintains the heat stability of the native enzyme. Recombinant *T. gorgonarius* polymerase has the same 3'-5'exonuclease activity as native *T. gorgonarius* polymerase, which is also sensitive to inhibition by an excess of dNTPs.

Example 5

Thermostability of *T. gorgonarius* DNA Polymerase

The thermostability of the DNA polymerase from *T. gorgonarius* purified as described in Example 1 was determined as follows: 5 units purified *T. gorgonarius* polymerase were incubated at 95° C. in 100 µl of the following buffer: 50 mM Tris-HCl, pH 8.8 (at 25° C.); 15 mM $(NH_4)_2SO_4$; 7 mM $MgCl_2$; 10 mM 2-mercaptoethanol; 200 µM each of dATP, dGTP, dCTP and dTTP; 01% NONIDET™ P40, 0.1% THESIT™; 25 µg DNAse treated calf thymus DNA. 15 µl samples were taken at 0, 5, 10, 15, 30, 45, 60 and 120 minutes. The remaining polymerase activity was measured as described in Example 4 by determining incorporation of labeled $^3$H-TTP into DNA in a 50 µl volume of the incubation mixture described above containing in addition 150 nCi of $^3$H-TTP. After incubation at 72° C. for 30 minutes, the reactions were stopped by addition of 300 µl 10% TCA, and after 10 minutes at 0° C. the mixtures were applied onto 3 MM filters (Whatman). The filters were washed three times with approximately 10 ml 5% TCA each time, dried for 10 minutes at 75° C. and the DNA-bound radioactivity of each filter was measured in 5 ml scintillation liquid in a scintillation vial in LKB rack beta 1217/1218 (Pharmacia).

Figure 4:
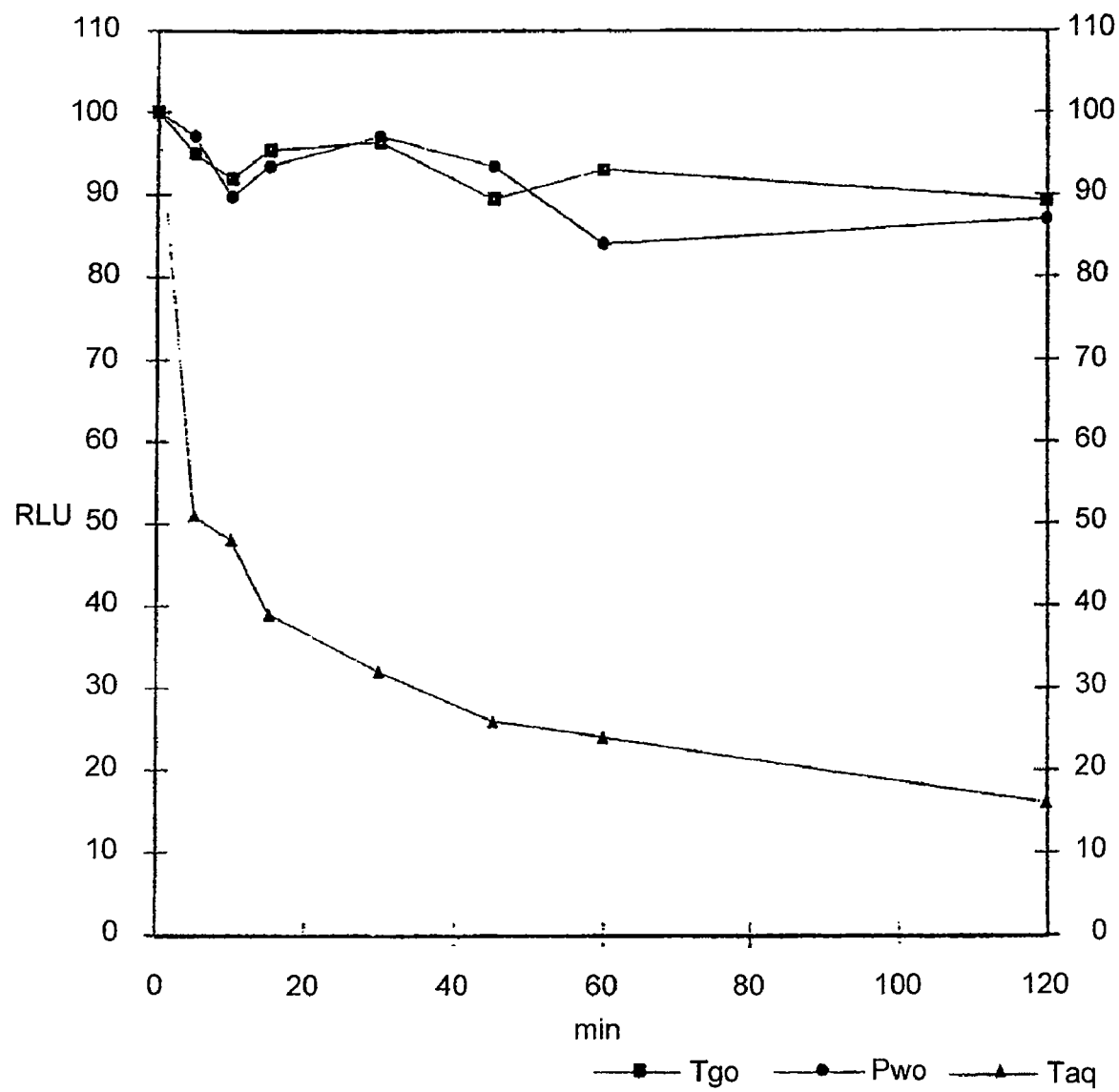

As shown in FIG. 4, the *T. gorgonarius* DNA polymerase retained almost 90% of its initial activity after incubation for 120 minutes at 95° C., Pwo polymerase has a similar stability, while Taq DNA polymerise has a remaining activity of approximately 16% only.

Example 6

Determination of 3'-5' Proofreading Activity

Figure 5:
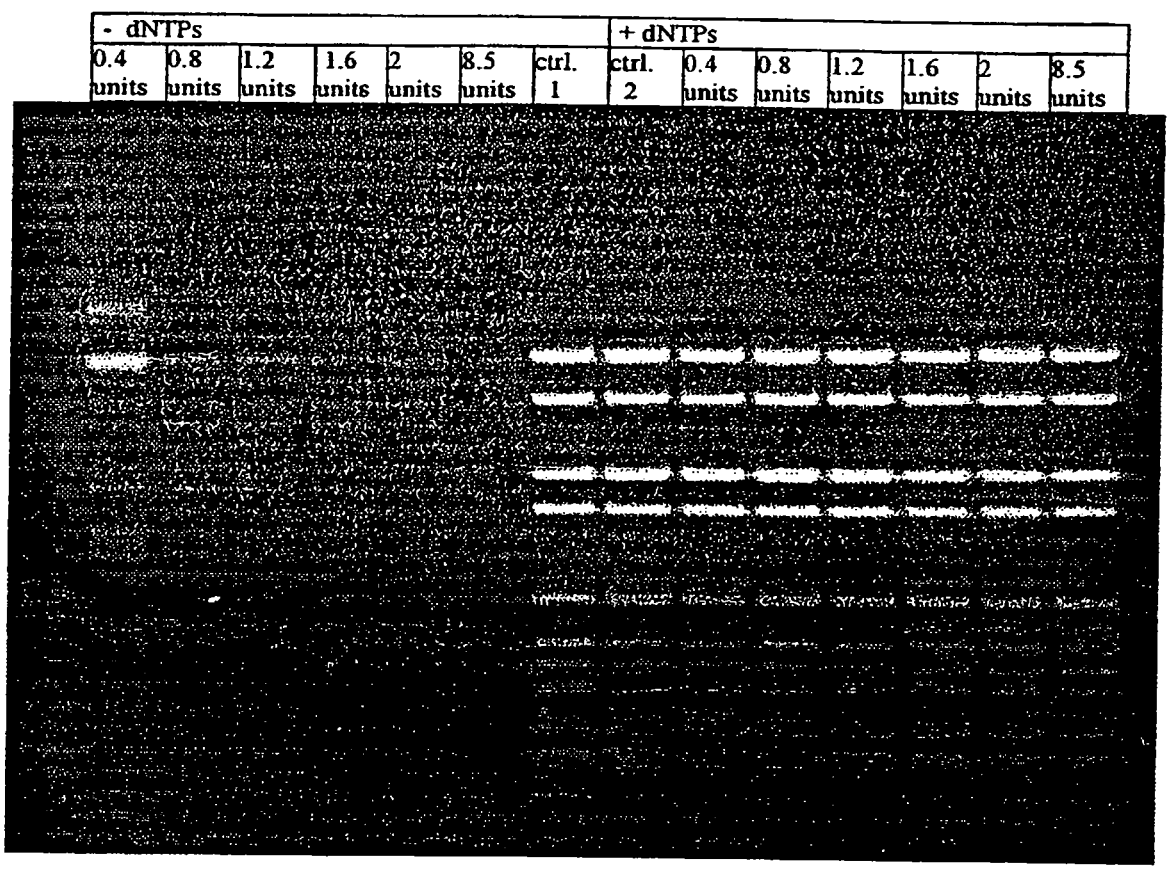
Figure 6:
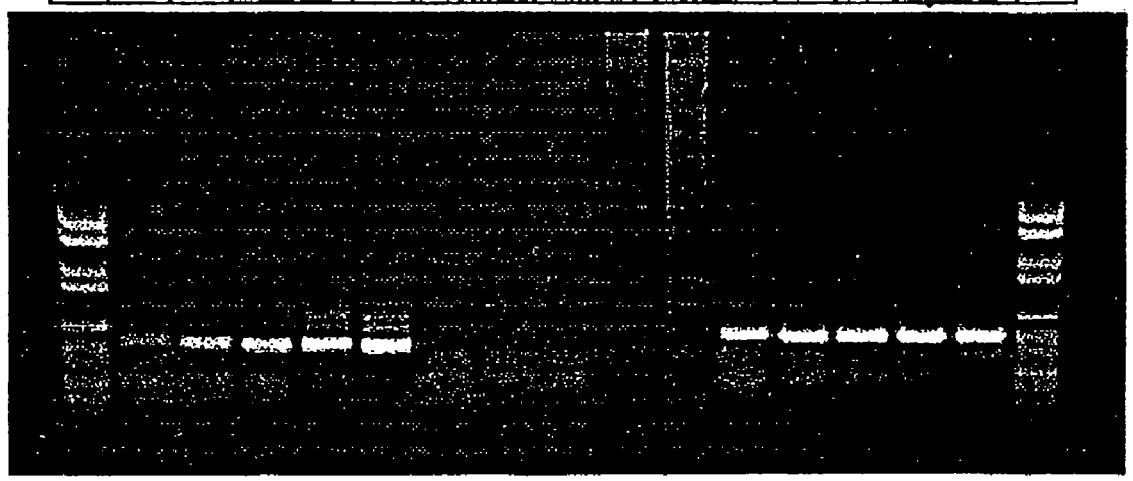
Figure 7:
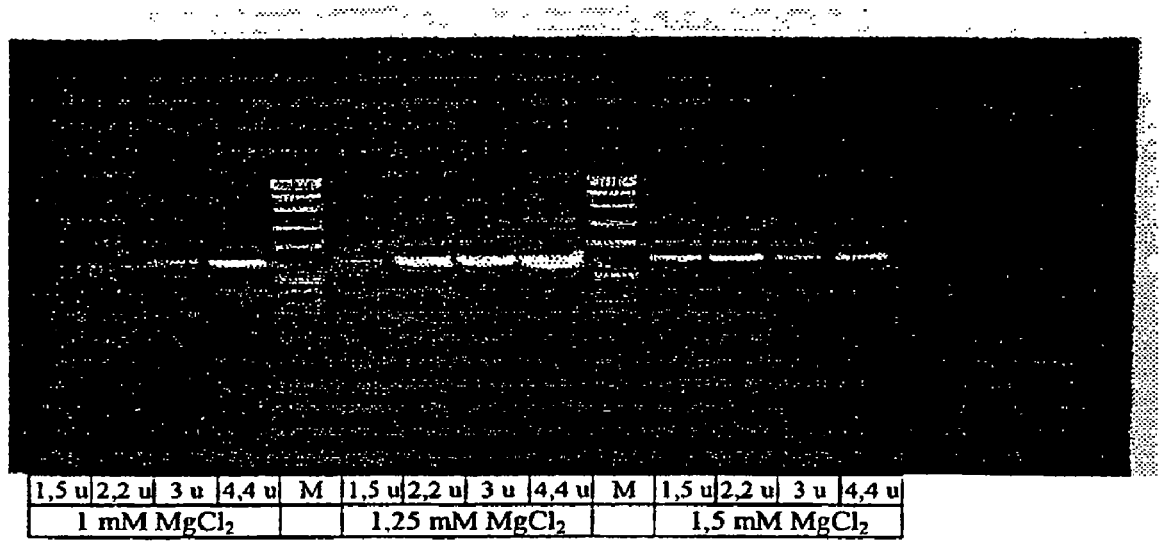
Figure 8:
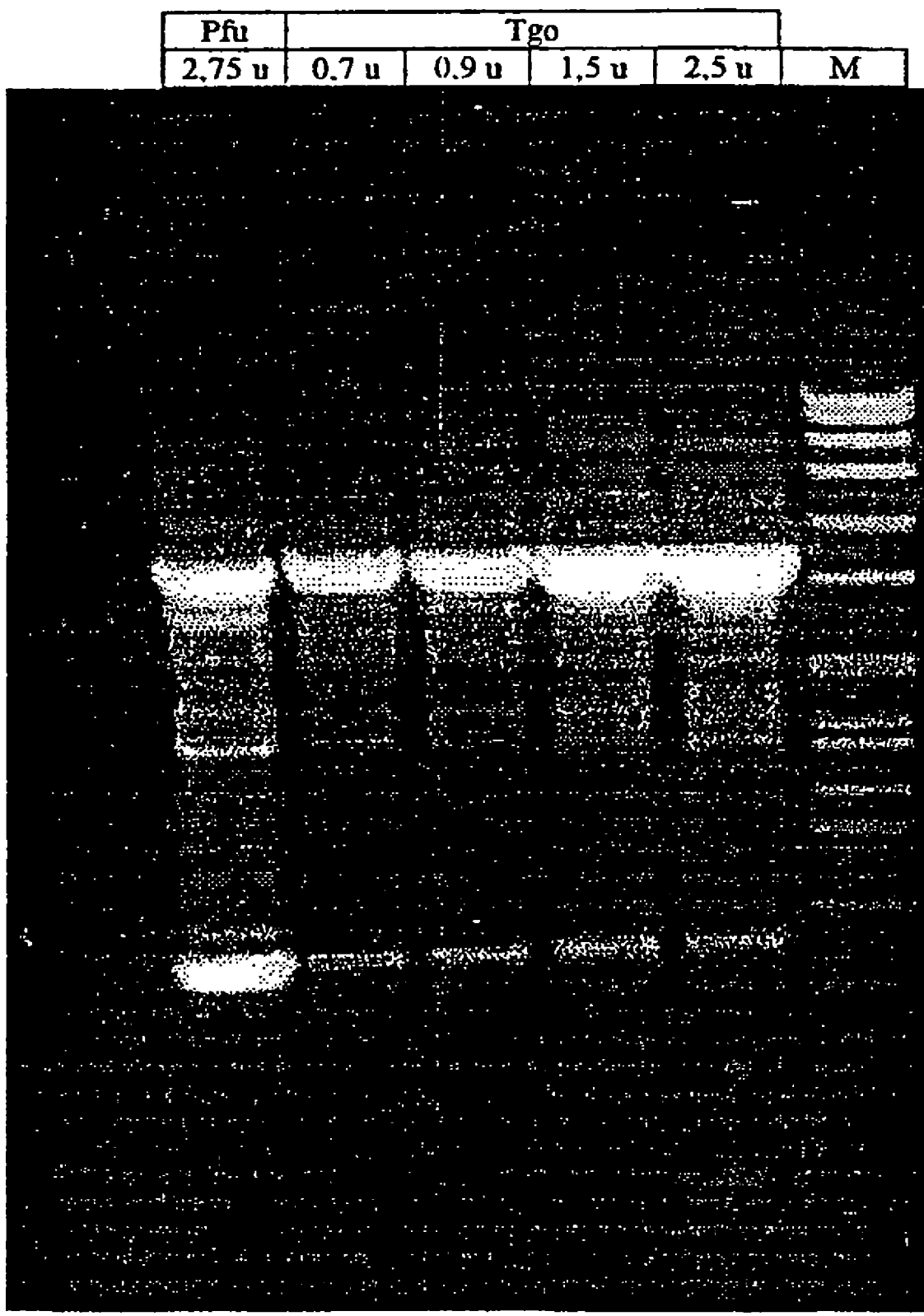
Figure 9:
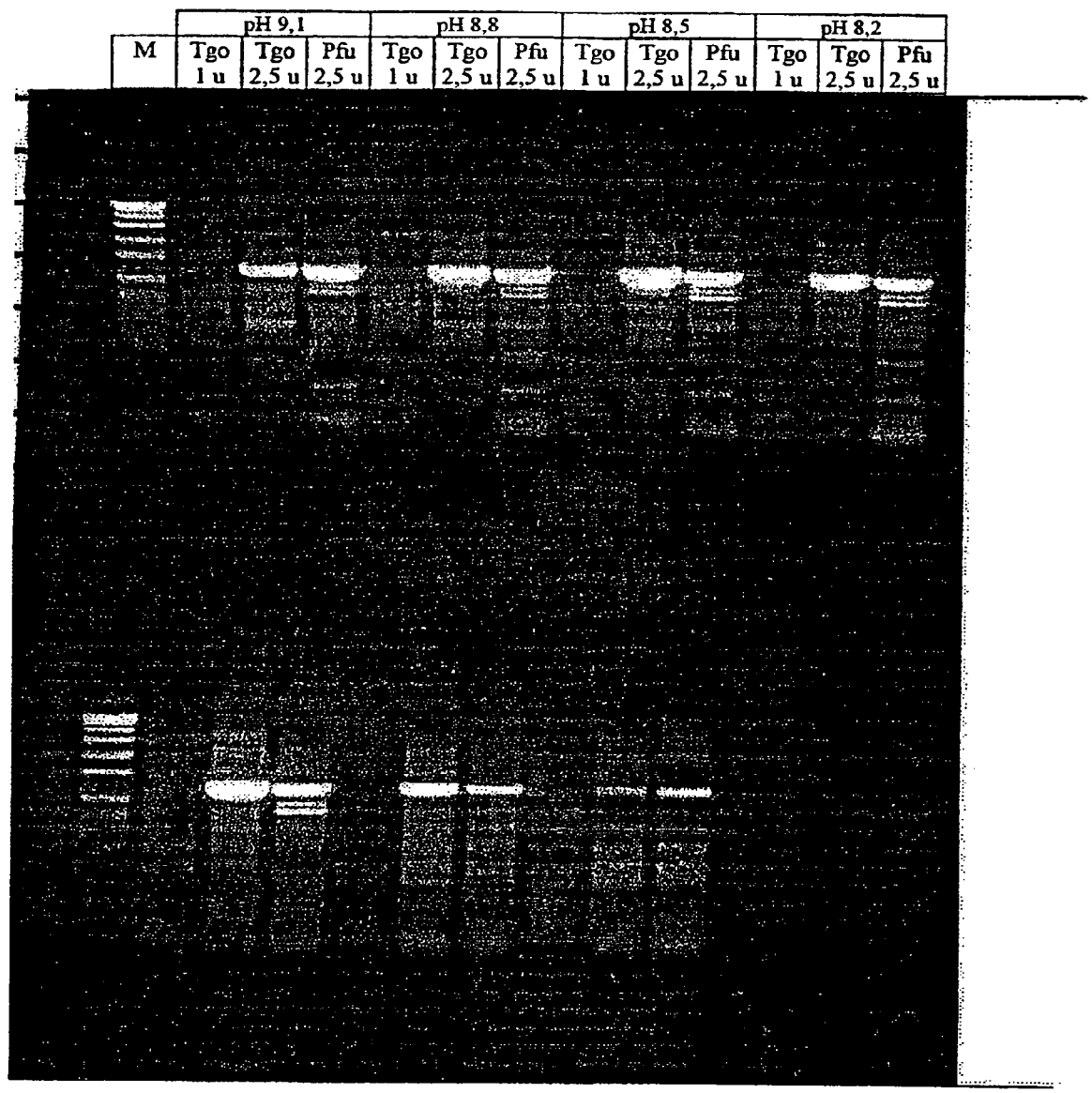
Figure 10:
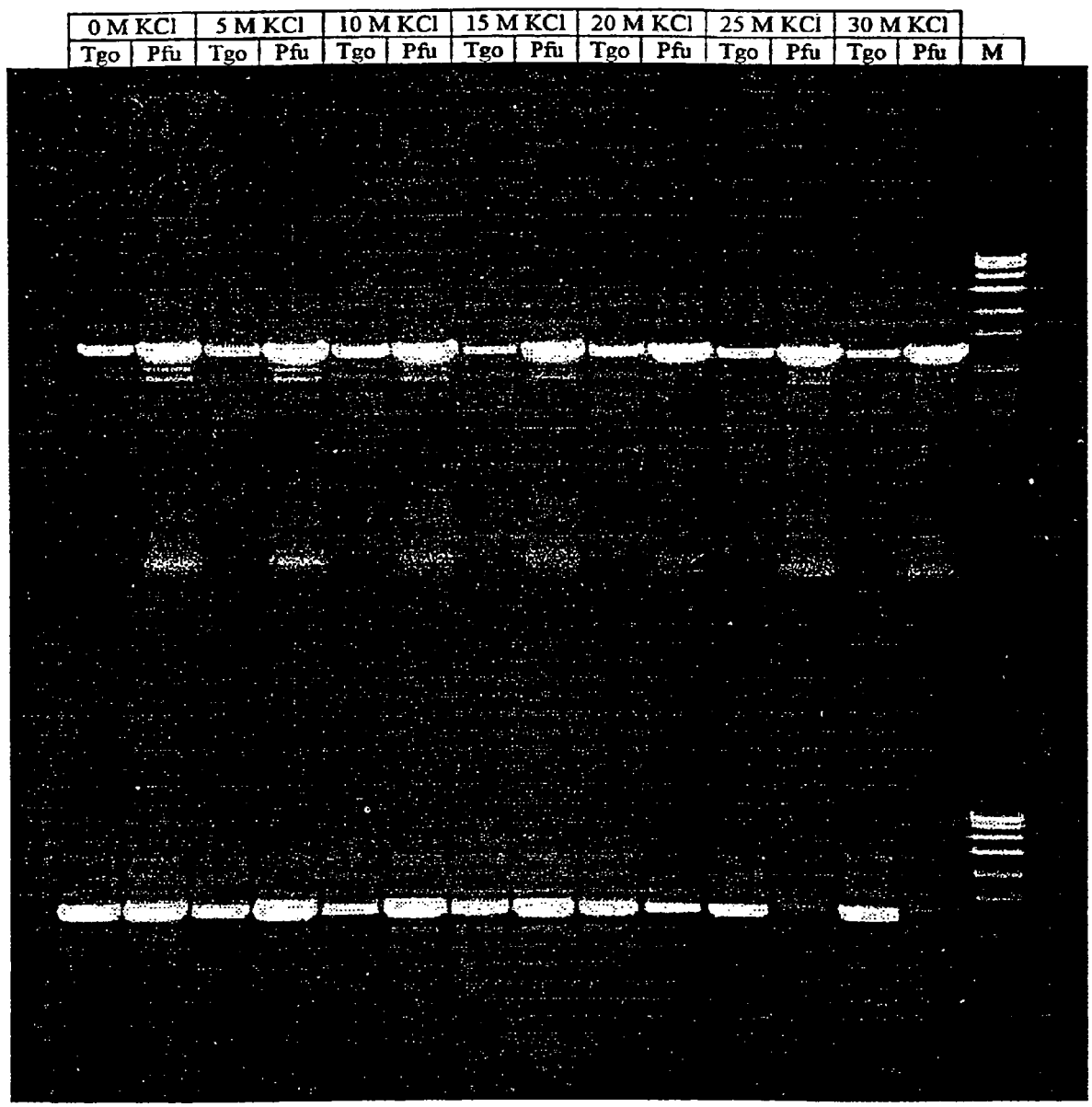

A series of units of *T. gorgonarius* DNA polymerase (see FIG. 5) were incubated for 4 hours at 72° C. with 1 µg DNA molecular weight marker VI (Boehringer Mannheim) in the presence and absence of dNTPs, 1 mM each, in 50 µl of the following incubation buffer: 50 mM Tris-HCl, pH 7.8; 10 mM $MgCl_2$; 7 mM 2-mercaptoethanol with Paraffin overlay. After addition of 10 µl stop solution the DNA fragments were separated on a 1% agarose gel. In the absence of dNTPs, a smear of DNA fragments or no DNA could be detected while in presence of dNTPs the DNA fragments remained undegraded.

Example 7

Fidelity of *T. gorgonarius* DNA Polymerase in the PCR Process

The fidelity of *T. gorgonarius* DNA polymerase in the PCR process was determined in an assay based on the amplification, circularization and transformation of the pUC19 derivate pUCIQ17, containing a functional lac I$^q$ allele (Frey, B. and Suppmann, B., *Biochemica*, 2:34-35 (1995)). PCR-derived mutations in lac I are resulting in a derepression of the expression of lac Zα and subsequent formation of a functional β-galactosidase enzyme which can be easily detected on X-Gal indicator plates. The error rates determined with this lac I-based PCR fidelity assay were in the range of 3.4 to $2.2 \cdot 10^{-6}$.

The plasmid pUCIQ17 was linearized by digestion with DraII to serve as a substrate for PCR amplification with DNA polymerase of *T. gorgonarius*. Both of the primers used have ClaI sites at their 5 prime ends:

```
SEQ ID NO: 8:
Primer 1:
5'-AGCTTATCGATGGCACTTTTCGGGGAAATGTGCG-3'

SEQ ID NO: 9:
Primer 2:
5'-AGCTTATCGATAAGCGGATGCCGGGAGCAGACAAGC-3'
```

The length of the resulting PCR product is 3493 pb.

The PCR was performed in a final volume of 50 µl in the presence of 1.5 mM MgCl$_2$, 50 mM Tris-HCl, pH 8.5 (25° C.), 12.5 mM (NH$_4$)$_2$SO$_4$, 35 mM KCl, 200 µM dNTPs and 2.5 units of *T. gorgonarius* DNA polymerase. Conditions of the amplification reaction using *T. gorgonarius* DNA polymerase are The cycle conditions were as follows:

1 × denaturation of template for 2 min. at 95° C.

8 × {
 denaturation at 95° C. for 10 sec.
 annealing at 57° C. for 30 sec.
 elongation at 72° C. for 4 min.
}

16 × {
 denaturation at 95° C. for 10 sec.
 annealing at 57° C. for 30 sec.
 elongation at 72° C. for 4 min. +
 cycle elongation of 20 sec. for each cycle
}

After PCR, the PCR products were PEG-precipitated (Barnes, W. M., *Gene*, 112:229 (1992)) the DNA restricted with ClaI and purified by agarose gel electrophoresis. The isolated DNA was ligated using the Rapid DNA Ligation Kit (Boehringer Mannheim GmbH) and the ligation products transformed in *E. coli* DH5α, plated on TN Amp X-Gal plates. The α-complementing *E. coli* strain DH5α transformed with the resulting plasmid pUCIQ17 (3632 bp), shows white (lacI$^+$) colonies on TN plates (1.5% Bacto Tryptone, 1% NaCl, 1.5% Agar) containing ampicillin (100 µg/ml) and X-Gal (0.004% w/v). Mutations result in blue colonies.

After incubation overnight at 37° C., blue and white colonies were counted. The error rate (f) per by was calculated with a rearranged equation as published by Keohavong and Thilly (Keohavong, P. and Thilly, W., *PNAS* USA, 86:9253 (1989)):

$$f = -\ln F/d \times b\ bp$$

where F is the fraction of white colonies:

$$F = \text{white}(lacI+) \text{ colonies/total colony number};$$

d is the number of DNA duplications:

$$2^d = \text{output DNA/input DNA};$$

and b is the effective target size of the (1080 bp) lac I gene, which is 349 bp according to Provost et al. (Provost et al., *Mut. Res.*, 288:133 (1993)).

Example 8

Fidelity Assay

Determination of the Misincorporation Rates of DNA Polymerases from *Pyrococcus furiosus* and *Thermococcus gorgonarius* under PCR Conditions.

Error rates of many DNA polymerases are published. For example for the DNA polymerase of *Pyrococcus furiosus* various error rates were measured (Lit. 1-5). They may vary with the conditions used, e.g., nucleotide triphosphate concentrations, enzyme preparation, buffer conditions and of course with the method used, the determination of the number of duplications and the way to calculate the misincorporation rate.

Therefore, the DNA polymerases Pfu (Stratagene) and Tgo (Boehringer Mannheim GmbH) were analyzed in parallel in the same system (Protocol: Frey, B. and Suppman, B. Boehringer Mannheim Biochemica Information, Nr. 96-1995, 21-23).

TABLE 1

Fidelity of Pfu and Tgo DNA polymerases in PCR fidelity assay

| DNA Polymerase | Plaques | Total scored Mutant | Mutation frequency | Error rate (a) | Error rate (b) |
|---|---|---|---|---|---|
| Pfu |
| 1. sample | 3082 | 76 | 2.47 | $1.56 \times 10^{-5}$ | $8.2 \times 10^{-6}$ |
| 2. sample | 2693 | 68 | 2.52 | $1.6 \times 10^{-5}$ | $8.4 \times 10^{-6}$ |
| Tgo |
| 1. sample | 1904 | 12 | 0.63 | $3.5 \times 10^{-6}$ | $1.8 \times 10^{-6}$ |
| 2. | 2003 | 20 | 1 | $5.6 \times 10^{-6}$ | $2.9 \times 10^{-6}$ |

(a) Error rate calculated according to the equation used by Stratagene (Lundberg, K. S. et al., Gene, 108: 1-6 (1991)).
ER = mf/bp × d
ER = error rate
mf = mutation frequency in % minus background frequency of 0.0017%
bp is the number of detectable sites in the lac I gene sequence (182)
d is the number of duplications. In this particular experiment the number of duplications was determined/estimated for Pfu to be 8.64 and for Tgo to be 9.64
(b) Error rate calculated per by with a rearranged equation published by Keohavong, P. and Thilly, W., PNAS USA, 86: 9253 (1989).
ER = −lnF/d × b bp
F = fraction of white colonies (white colonies/total number of colonies)
d = the number of duplications. $2^d$ = output DNA/input DNA
b is the effective target size of the (1080 bp) lac I gene, which is 349 bp according to Provost, G. S. et al., Mut. Res., 288: 133 (1993)

Result:

These data show that the mutation frequency of Tgo DNA polymerase is lower than that of Pfu, and the fidelity (calculated in errors per base pair) is higher no matter which way of calculation was used.

REFERENCE DESCRIBING ERROR RATES FOR Pfu

1. Lundberg, K. S. et al., *Gene*, 108:1-6 (1991) ($1.6 \times 10^{-6}$ errors/base)
2. Flaman, J. M. et al., *NAR*, 22:3259-3260 (1994). ($2 \times 10^{-6}$ errors/base) For Tli (Vent) Polymerase: (Variations in error rate depending on assay)
3. Cariello, N. F. et al., *NAR*, 19:4193-4198 (1991). ($2.4 \times 10^{-5}$ errors/base)
4. Ling, L. L. et al., *PCR Methods Appl.*, 1:63-69 (1991). ($4.5 \times 10^{-5}$ errors/base)
5. Matilla, P. et al., *NAR*, 19:4967-4973 (1991). ($5.7 \times 10^{-5}$ errors/base)

The invention claimed is:

1. An isolated DNA encoding a thermostable DNA polymerase obtainable from *Thermococcus gorgonarius* which catalyses the template directed polymerization of DNA, possesses 3'-5'-exonuclease (proofreading) activity and is characterized by at least a two-fold greater replication fidelity than DNA polymerase obtainable from *Pyrococcus furiosus*, wherein:
the DNA polymerase comprises the amino acid sequence set forth in SEQ ID NO:7; or
the isolated DNA comprises the nucleotide sequence set forth in SEQ ID NO:6; or
the DNA polymerase has an apparent molecular weight between about 92,000 and 96,000 daltons.

2. The isolated DNA of claim 1, wherein the DNA polymerase comprises the amino acid sequence set forth in SEQ ID NO:7.

3. The isolated DNA of claim 1, wherein the DNA comprises the nucleotide sequence set forth in SEQ ID NO:6.

4. The isolated DNA of claim 1, wherein the DNA polymerase has an apparent molecular weight between about 92,000 and 96,000 daltons.

5. A vector comprising the DNA sequence of claim 1.

6. The vector of claim 5, wherein the DNA polymerase comprises the amino acid sequence set forth in SEQ ID NO:7.

7. The vector of claim 5, wherein the DNA comprises the nucleotide sequence set forth in SEQ ID NO:6.

8. The vector of claim 5, wherein the DNA polymerase has an apparent molecular weight between about 92,000 and 96,000 daltons.

9. A microbial host cell transformed with the vector of claim 5.

10. The microbial host cell of claim 9, wherein the DNA polymerase comprises the amino acid sequence set forth in SEQ ID NO:7.

11. The microbial host cell of claim 9, wherein the DNA comprises the nucleotide sequence set forth in SEQ ID NO:6.

12. The microbial host cell of claim 9, wherein the DNA polymerase has an apparent molecular weight between about 92,000 and 96,000 daltons.

13. The microbial host cell of claim 9, wherein the host cell is *E. coli*.

* * * * *

SEQUENCE LISTING

<160> NUMBER OF SEQ ID NOS: 9

<210> SEQ ID NO 1
<211> LENGTH: 26
<212> TYPE: DNA
<213> ORGANISM: Artificial
<220> FEATURE:
<223> OTHER INFORMATION: probe
<220> FEATURE:
<221> NAME/KEY: misc_feature
<222> LOCATION: (9)..(9)
<223> OTHER INFORMATION: any nucleotide
<220> FEATURE:
<221> NAME/KEY: misc_feature
<222> LOCATION: (15)..(15)
<223> OTHER INFORMATION: any nucleotide

<400> SEQUENCE: 1
atgathytng ayacngayta yathac                                          26

<210> SEQ ID NO 2
<211> LENGTH: 24
<212> TYPE: DNA
<213> ORGANISM: Artificial
<220> FEATURE:
<223> OTHER INFORMATION: amplification primer

<400> SEQUENCE: 2
ggcctacgag aggaacgaac tggc                                            24

<210> SEQ ID NO 3
<211> LENGTH: 18
<212> TYPE: DNA
<213> ORGANISM: Artificial
<220> FEATURE:
<223> OTHER INFORMATION: amplification primer

<400> SEQUENCE: 3
ggcgtagatg tagggctc                                                   18

<210> SEQ ID NO 4
<211> LENGTH: 42
<212> TYPE: DNA
<213> ORGANISM: Artificial
<220> FEATURE:
<223> OTHER INFORMATION: amplification primer

<400> SEQUENCE: 4
gagctggtcg aattcatgat cctggacgct gactacatca cc                        42

<210> SEQ ID NO 5
<211> LENGTH: 33
<212> TYPE: DNA
<213> ORGANISM: Artificial
<220> FEATURE:
<223> OTHER INFORMATION: amplification primer

<400> SEQUENCE: 5
agcctgcagt catgtcttag gttttagcca cgc                                  33

<210> SEQ ID NO 6
<211> LENGTH: 2322
<212> TYPE: DNA
<213> ORGANISM: Thermococcus gorgonarius
<220> FEATURE:
<221> NAME/KEY: CDS -continued

<222> LOCATION: (1)..(2322)

<400> SEQUENCE: 6

| | | | | | | | | | | | | | | | | |
|---|---|---|---|---|---|---|---|---|---|---|---|---|---|---|---|---|
| atg | atc | ctc | gat | aca | gac | tac | ata | act | gag | gat | gga | aag | ccc | gtc | atc | 48 |
| Met | Ile | Leu | Asp | Thr | Asp | Tyr | Ile | Thr | Glu | Asp | Gly | Lys | Pro | Val | Ile | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| agg | atc | ttc | aag | aag | gag | aac | ggc | gag | ttc | acc | ata | gac | tac | gac | aga | 96 |
| Arg | Ile | Phe | Lys | Lys | Glu | Asn | Gly | Glu | Phe | Thr | Ile | Asp | Tyr | Asp | Arg | |
| | | | 20 | | | | | 25 | | | | | 30 | | | |

| | | | | | | | | | | | | | | | | |
|---|---|---|---|---|---|---|---|---|---|---|---|---|---|---|---|---|
| aac | ttt | gag | cca | tac | atc | tac | gcg | ctc | ttg | aag | gac | gac | tct | ccg | att | 144 |
| Asn | Phe | Glu | Pro | Tyr | Ile | Tyr | Ala | Leu | Leu | Lys | Asp | Asp | Ser | Pro | Ile | |
| | | | | 35 | | | | 40 | | | | | 45 | | | |

| | | | | | | | | | | | | | | | | |
|---|---|---|---|---|---|---|---|---|---|---|---|---|---|---|---|---|
| gag | gac | gtc | aag | aag | ata | act | gcc | gag | agg | cac | ggc | act | acc | gtt | agg | 192 |
| Glu | Asp | Val | Lys | Lys | Ile | Thr | Ala | Glu | Arg | His | Gly | Thr | Thr | Val | Arg | |
| | | 50 | | | | | 55 | | | | | 60 | | | | |

| | | | | | | | | | | | | | | | | |
|---|---|---|---|---|---|---|---|---|---|---|---|---|---|---|---|---|
| gtt | gtc | agg | gcc | gag | aaa | gtg | aag | aag | aag | ttc | cta | ggc | agg | ccg | ata | 240 |
| Val | Val | Arg | Ala | Glu | Lys | Val | Lys | Lys | Lys | Phe | Leu | Gly | Arg | Pro | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gag | gtc | tgg | aag | ctc | tac | ttc | act | cac | ccc | cag | gac | gtt | ccc | gca | atc | 288 |
| Glu | Val | Trp | Lys | Leu | Tyr | Phe | Thr | His | Pro | Gln | Asp | Val | Pro | Ala | Ile | |
| | | | | 85 | | | | | 90 | | | | | 95 | | |

| | | | | | | | | | | | | | | | | |
|---|---|---|---|---|---|---|---|---|---|---|---|---|---|---|---|---|
| agg | gac | aag | ata | aag | gag | cat | cct | gcc | gtt | gtg | gac | atc | tac | gag | tac | 336 |
| Arg | Asp | Lys | Ile | Lys | Glu | His | Pro | Ala | Val | Val | Asp | Ile | Tyr | Glu | Tyr | |
| | | | | 100 | | | | | 105 | | | | | 110 | | |

| | | | | | | | | | | | | | | | | |
|---|---|---|---|---|---|---|---|---|---|---|---|---|---|---|---|---|
| gac | atc | ccc | ttc | gcg | aag | cgc | tac | ctc | ata | gac | aaa | ggc | tta | atc | ccg | 384 |
| Asp | Ile | Pro | Phe | Ala | Lys | Arg | Tyr | Leu | Ile | Asp | Lys | Gly | Leu | Ile | Pro | |
| | | | 115 | | | | | 120 | | | | | 125 | | | |

| | | | | | | | | | | | | | | | | |
|---|---|---|---|---|---|---|---|---|---|---|---|---|---|---|---|---|
| atg | gag | ggc | gac | gag | gaa | ctt | aag | atg | ctc | gcc | ttc | gac | atc | gag | acg | 432 |
| Met | Glu | Gly | Asp | Glu | Glu | Leu | Lys | Met | Leu | Ala | Phe | Asp | Ile | Glu | Thr | |
| | | 130 | | | | | 135 | | | | | 140 | | | | |

| | | | | | | | | | | | | | | | | |
|---|---|---|---|---|---|---|---|---|---|---|---|---|---|---|---|---|
| ctc | tat | cac | gag | ggc | gag | gag | ttc | gcc | gaa | ggg | cct | atc | ctg | atg | ata | 480 |
| Leu | Tyr | His | Glu | Gly | Glu | Glu | Phe | Ala | Glu | Gly | Pro | Ile | Leu | Met | Ile | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| agc | tac | gcc | gac | gag | gaa | ggg | gcg | cgc | gtt | att | acc | tgg | aag | aat | atc | 528 |
| Ser | Tyr | Ala | Asp | Glu | Glu | Gly | Ala | Arg | Val | Ile | Thr | Trp | Lys | Asn | Ile | |
| | | | | 165 | | | | | 170 | | | | | 175 | | |

| | | | | | | | | | | | | | | | | |
|---|---|---|---|---|---|---|---|---|---|---|---|---|---|---|---|---|
| gac | ctt | ccc | tat | gtc | gac | gtc | gtt | tcc | acc | gag | aag | gag | atg | ata | aag | 576 |
| Asp | Leu | Pro | Tyr | Val | Asp | Val | Val | Ser | Thr | Glu | Lys | Glu | Met | Ile | Lys | |
| | | | | 180 | | | | | 185 | | | | | 190 | | |

| | | | | | | | | | | | | | | | | |
|---|---|---|---|---|---|---|---|---|---|---|---|---|---|---|---|---|
| cgc | ttc | ctc | aag | gtc | gtc | aag | gaa | aag | gat | ccc | gac | gtc | ctc | ata | atc | 624 |
| Arg | Phe | Leu | Lys | Val | Val | Lys | Glu | Lys | Asp | Pro | Asp | Val | Leu | Ile | Ile | |
| | | | 195 | | | | | 200 | | | | | 205 | | | |

| | | | | | | | | | | | | | | | | |
|---|---|---|---|---|---|---|---|---|---|---|---|---|---|---|---|---|
| tac | aac | ggc | gac | aac | ttc | gac | ttc | gcc | tac | ctc | aag | aag | cgc | tcc | gag | 672 |
| Tyr | Asn | Gly | Asp | Asn | Phe | Asp | Phe | Ala | Tyr | Leu | Lys | Lys | Arg | Ser | Glu | |
| | | 210 | | | | | 215 | | | | | 220 | | | | |

| | | | | | | | | | | | | | | | | |
|---|---|---|---|---|---|---|---|---|---|---|---|---|---|---|---|---|
| aag | ctc | gga | gtc | aag | ttc | atc | ctc | gga | agg | gaa | ggg | agc | gaa | ccg | aaa | 720 |
| Lys | Leu | Gly | Val | Lys | Phe | Ile | Leu | Gly | Arg | Glu | Gly | Ser | Glu | Pro | Lys | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| atc | cag | cgc | atg | ggc | gat | cgc | ttt | gcg | gtg | gag | gtc | aag | gga | agg | att | 768 |
| Ile | Gln | Arg | Met | Gly | Asp | Arg | Phe | Ala | Val | Glu | Val | Lys | Gly | Arg | Ile | |
| | | | | 245 | | | | | 250 | | | | | 255 | | |

| | | | | | | | | | | | | | | | | |
|---|---|---|---|---|---|---|---|---|---|---|---|---|---|---|---|---|
| cac | ttc | gac | ctc | tac | ccc | gtc | att | agg | aga | acg | att | aac | ctc | ccc | act | 816 |
| His | Phe | Asp | Leu | Tyr | Pro | Val | Ile | Arg | Arg | Thr | Ile | Asn | Leu | Pro | Thr | |
| | | | | 260 | | | | | 265 | | | | | 270 | | |

| | | | | | | | | | | | | | | | | |
|---|---|---|---|---|---|---|---|---|---|---|---|---|---|---|---|---|
| tac | acc | ctt | gag | gca | gta | tat | gaa | gcc | atc | ttt | gga | cag | ccg | aag | gag | 864 |
| Tyr | Thr | Leu | Glu | Ala | Val | Tyr | Glu | Ala | Ile | Phe | Gly | Gln | Pro | Lys | Glu | |
| | | | 275 | | | | | 280 | | | | | 285 | | | |

| | | | | | | | | | | | | | | | | |
|---|---|---|---|---|---|---|---|---|---|---|---|---|---|---|---|---|
| aag | gtc | tac | gct | gag | gag | ata | gcg | cag | gcc | tgg | gaa | acg | ggc | gag | gga | 912 |
| Lys | Val | Tyr | Ala | Glu | Glu | Ile | Ala | Gln | Ala | Trp | Glu | Thr | Gly | Glu | Gly | |
| | | 290 | | | | | 295 | | | | | 300 | | | | |

| | | | | | | | | | | | | | | | | |
|---|---|---|---|---|---|---|---|---|---|---|---|---|---|---|---|---|
| tta | gaa | agg | gtg | gcc | cgc | tac | tcg | atg | gag | gac | gcg | aag | gta | acc | tat | 960 |
| Leu | Glu | Arg | Val | Ala | Arg | Tyr | Ser | Met | Glu | Asp | Ala | Lys | Val | Thr | Tyr | |
| 305 | | | | 310 | | | | | 315 | | | | | 320 | | |
| gaa | ctc | gga | aaa | gag | ttc | ttc | cct | atg | gaa | gcc | cag | ctc | tcg | cgc | ctc | 1008 |
| Glu | Leu | Gly | Lys | Glu | Phe | Phe | Pro | Met | Glu | Ala | Gln | Leu | Ser | Arg | Leu | |
| | | | | 325 | | | | | 330 | | | | | 335 | | |
| gta | ggc | cag | agc | ctc | tgg | gat | gta | tct | cgc | tcg | agt | acc | gga | aac | ctc | 1056 |
| Val | Gly | Gln | Ser | Leu | Trp | Asp | Val | Ser | Arg | Ser | Ser | Thr | Gly | Asn | Leu | |
| | | | 340 | | | | | 345 | | | | | 350 | | | |
| gtc | gag | tgg | ttt | ttg | ctg | agg | aag | gcc | tac | gag | agg | aat | gaa | ctt | gca | 1104 |
| Val | Glu | Trp | Phe | Leu | Leu | Arg | Lys | Ala | Tyr | Glu | Arg | Asn | Glu | Leu | Ala | |
| | | 355 | | | | | 360 | | | | | 365 | | | | |
| cca | aac | aag | ccg | gac | gag | agg | gag | ctg | gca | aga | aga | agg | gag | agc | tac | 1152 |
| Pro | Asn | Lys | Pro | Asp | Glu | Arg | Glu | Leu | Ala | Arg | Arg | Arg | Glu | Ser | Tyr | |
| | 370 | | | | | 375 | | | | | 380 | | | | | |
| gcg | ggt | gga | tac | gtc | aag | gag | ccc | gaa | agg | gga | ctg | tgg | gag | aac | atc | 1200 |
| Ala | Gly | Gly | Tyr | Val | Lys | Glu | Pro | Glu | Arg | Gly | Leu | Trp | Glu | Asn | Ile | |
| 385 | | | | 390 | | | | | 395 | | | | | 400 | | |
| gtg | tat | ctg | gac | ttc | cgc | tcc | ctg | tat | cct | tcg | ata | ata | atc | acc | cat | 1248 |
| Val | Tyr | Leu | Asp | Phe | Arg | Ser | Leu | Tyr | Pro | Ser | Ile | Ile | Ile | Thr | His | |
| | | | | 405 | | | | | 410 | | | | | 415 | | |
| aac | gtc | tcc | cct | gat | aca | ctc | aac | agg | gag | ggt | tgt | gag | gag | tac | gac | 1296 |
| Asn | Val | Ser | Pro | Asp | Thr | Leu | Asn | Arg | Glu | Gly | Cys | Glu | Glu | Tyr | Asp | |
| | | | 420 | | | | | 425 | | | | | 430 | | | |
| gtg | gct | cct | cag | gta | ggc | cat | aag | ttc | tgc | aag | gac | ttc | ccc | ggc | ttc | 1344 |
| Val | Ala | Pro | Gln | Val | Gly | His | Lys | Phe | Cys | Lys | Asp | Phe | Pro | Gly | Phe | |
| | | 435 | | | | | 440 | | | | | 445 | | | | |
| atc | cca | agc | ctc | ctc | gga | gac | ctc | ttg | gag | gag | aga | cag | aag | gta | aag | 1392 |
| Ile | Pro | Ser | Leu | Leu | Gly | Asp | Leu | Leu | Glu | Glu | Arg | Gln | Lys | Val | Lys | |
| | 450 | | | | | 455 | | | | | 460 | | | | | |
| aag | aag | atg | aag | gcc | act | ata | gac | cca | atc | gag | aag | aaa | ctc | ctc | gat | 1440 |
| Lys | Lys | Met | Lys | Ala | Thr | Ile | Asp | Pro | Ile | Glu | Lys | Lys | Leu | Leu | Asp | |
| 465 | | | | 470 | | | | | 475 | | | | | 480 | | |
| tac | agg | caa | cga | gca | atc | aaa | atc | ctt | gct | aat | agc | ttc | tac | ggt | tac | 1488 |
| Tyr | Arg | Gln | Arg | Ala | Ile | Lys | Ile | Leu | Ala | Asn | Ser | Phe | Tyr | Gly | Tyr | |
| | | | | 485 | | | | | 490 | | | | | 495 | | |
| tac | ggc | tat | aca | aag | gcc | cgc | tgg | tac | tac | aag | gag | tgc | gcc | gag | agc | 1536 |
| Tyr | Gly | Tyr | Thr | Lys | Ala | Arg | Trp | Tyr | Tyr | Lys | Glu | Cys | Ala | Glu | Ser | |
| | | | 500 | | | | | 505 | | | | | 510 | | | |
| gtt | acc | ggt | tgg | ggc | agg | gag | tac | atc | gag | acc | acg | ata | agg | gaa | ata | 1584 |
| Val | Thr | Gly | Trp | Gly | Arg | Glu | Tyr | Ile | Glu | Thr | Thr | Ile | Arg | Glu | Ile | |
| | | 515 | | | | | 520 | | | | | 525 | | | | |
| gag | gag | aaa | ttt | ggc | ttt | aaa | gtc | ctc | tac | gcg | gac | aca | gat | gga | ttt | 1632 |
| Glu | Glu | Lys | Phe | Gly | Phe | Lys | Val | Leu | Tyr | Ala | Asp | Thr | Asp | Gly | Phe | |
| | 530 | | | | | 535 | | | | | 540 | | | | | |
| ttc | gca | aca | ata | cct | gga | gcg | gac | gcc | gaa | acc | gtc | aaa | aag | aag | gca | 1680 |
| Phe | Ala | Thr | Ile | Pro | Gly | Ala | Asp | Ala | Glu | Thr | Val | Lys | Lys | Lys | Ala | |
| 545 | | | | 550 | | | | | 555 | | | | | 560 | | |
| aag | gag | ttc | ctg | gac | tac | atc | aac | gcc | aaa | ctg | ccc | ggc | ctg | ctc | gaa | 1728 |
| Lys | Glu | Phe | Leu | Asp | Tyr | Ile | Asn | Ala | Lys | Leu | Pro | Gly | Leu | Leu | Glu | |
| | | | | 565 | | | | | 570 | | | | | 575 | | |
| ctc | gaa | tac | gag | ggc | ttc | tac | aag | cgc | ggc | ttc | ttc | gtg | acg | aag | aag | 1776 |
| Leu | Glu | Tyr | Glu | Gly | Phe | Tyr | Lys | Arg | Gly | Phe | Phe | Val | Thr | Lys | Lys | |
| | | | 580 | | | | | 585 | | | | | 590 | | | |
| aag | tac | gcg | gtt | ata | gac | gag | gag | gac | aag | ata | acg | acg | cgc | ggg | ctt | 1824 |
| Lys | Tyr | Ala | Val | Ile | Asp | Glu | Glu | Asp | Lys | Ile | Thr | Thr | Arg | Gly | Leu | |
| | | 595 | | | | | 600 | | | | | 605 | | | | |
| gaa | ata | gtt | agg | cgt | gac | tgg | agc | gag | ata | gcg | aag | gag | acg | cag | gcg | 1872 |
| Glu | Ile | Val | Arg | Arg | Asp | Trp | Ser | Glu | Ile | Ala | Lys | Glu | Thr | Gln | Ala | |

```
              610                 615                 620
agg gtt ctt gag gcg ata cta aag cac ggt gac gtt gaa gaa gcg gta    1920
Arg Val Leu Glu Ala Ile Leu Lys His Gly Asp Val Glu Glu Ala Val
625                 630                 635                 640 agg att gtc aaa gag gtt acg gag aag ctg agc aag tac gag gtt cca    1968
Arg Ile Val Lys Glu Val Thr Glu Lys Leu Ser Lys Tyr Glu Val Pro
            645                 650                 655 ccg gag aag ctg gtc atc tac gag cag ata acc cgc gac ctg aag gac    2016
Pro Glu Lys Leu Val Ile Tyr Glu Gln Ile Thr Arg Asp Leu Lys Asp
        660                 665                 670 tac aag gcc acc ggg ccg cat gtg gct gtt gca aaa cgc ctc gcc gca    2064
Tyr Lys Ala Thr Gly Pro His Val Ala Val Ala Lys Arg Leu Ala Ala
    675                 680                 685 agg ggg ata aaa atc cgg ccc gga acg gtc ata agc tac atc gtg ctc    2112
Arg Gly Ile Lys Ile Arg Pro Gly Thr Val Ile Ser Tyr Ile Val Leu
690                 695                 700 aaa ggc tcg gga agg att ggg gac agg gct ata ccc ttt gac gaa ttt    2160
Lys Gly Ser Gly Arg Ile Gly Asp Arg Ala Ile Pro Phe Asp Glu Phe
705                 710                 715                 720 gac ccg gca aag cac aag tac gat gca gaa tac tac atc gag aac cag    2208
Asp Pro Ala Lys His Lys Tyr Asp Ala Glu Tyr Tyr Ile Glu Asn Gln
            725                 730                 735 gtt ctt cca gct gtg gag agg att ctg agg gcc ttt ggt tac cgt aaa    2256
Val Leu Pro Ala Val Glu Arg Ile Leu Arg Ala Phe Gly Tyr Arg Lys
        740                 745                 750 gaa gat tta agg tat cag aaa acg cgg cag gtt ggc ttg ggg gcg tgg    2304
Glu Asp Leu Arg Tyr Gln Lys Thr Arg Gln Val Gly Leu Gly Ala Trp
    755                 760                 765 cta aaa cct aag aca tga                                            2322
Leu Lys Pro Lys Thr
770

<210> SEQ ID NO 7
<211> LENGTH: 773
<212> TYPE: PRT
<213> ORGANISM: Thermococcus gorgonarius

<400> SEQUENCE: 7

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Thr Ile Asp Tyr Asp Arg
            20                  25                  30

Asn Phe Glu Pro Tyr Ile Tyr Ala Leu Leu Lys Asp Asp Ser Pro Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160
```

-continued

Ser Tyr Ala Asp Glu Glu Gly Ala Arg Val Ile Thr Trp Lys Asn Ile
            165                 170                 175

Asp Leu Pro Tyr Val Asp Val Ser Thr Glu Lys Glu Met Ile Lys
        180                 185                 190

Arg Phe Leu Lys Val Val Lys Glu Lys Asp Pro Asp Val Leu Ile Ile
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Thr Lys Ala Arg Trp Tyr Tyr Lys Glu Cys Ala Glu Ser
            500                 505                 510

Val Thr Gly Trp Gly Arg Glu Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

```
Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770

<210> SEQ ID NO 8
<211> LENGTH: 34
<212> TYPE: DNA
<213> ORGANISM: Artificial
<220> FEATURE:
<223> OTHER INFORMATION: amplification primer

<400> SEQUENCE: 8
agcttatcga tggcactttt cggggaaatg tgcg                                34

<210> SEQ ID NO 9
<211> LENGTH: 36
<212> TYPE: DNA
<213> ORGANISM: Artificial
<220> FEATURE:
<223> OTHER INFORMATION: amplification primer

<400> SEQUENCE: 9
agcttatcga taagcggatg ccgggagcag acaagc                              36
```